United States Patent
Zhu

(10) Patent No.: US 10,544,460 B2
(45) Date of Patent: Jan. 28, 2020

(54) HOMEOBOX TRANSCRIPTION FACTOR VENTX REGULATES DIFFERENTIATION AND MATURATION OF HUMAN DENDRITIC CELLS

(71) Applicant: Zhenglun Zhu, Newton, MA (US)

(72) Inventor: Zhenglun Zhu, Newton, MA (US)

(73) Assignee: Zhenglun Zhu, Newton, MA (US)

( * ) Notice: Subject to any disclaimer, the term of this patent is extended or adjusted under 35 U.S.C. 154(b) by 396 days.

(21) Appl. No.: 14/781,359

(22) PCT Filed: Apr. 10, 2014

(86) PCT No.: PCT/US2014/033577
§ 371 (c)(1),
(2) Date: Sep. 30, 2015

(87) PCT Pub. No.: WO2014/169086
PCT Pub. Date: Oct. 16, 2014

(65) Prior Publication Data
US 2016/0068908 A1    Mar. 10, 2016

Related U.S. Application Data

(60) Provisional application No. 61/810,610, filed on Apr. 10, 2013.

(51) Int. Cl.
| | | |
|---|---|---|
| *C12N 5/00* | (2006.01) |
| *C12Q 1/6883* | (2018.01) |
| *A61K 38/17* | (2006.01) |
| *C07K 16/18* | (2006.01) |
| *C12N 15/113* | (2010.01) |
| *G01N 33/50* | (2006.01) |
| *G01N 33/564* | (2006.01) |

(52) U.S. Cl.
CPC ........ *C12Q 1/6883* (2013.01); *A61K 38/1709* (2013.01); *C07K 16/18* (2013.01); *C12N 15/113* (2013.01); *G01N 33/5023* (2013.01); *G01N 33/564* (2013.01); *C07K 2317/76* (2013.01); *C12N 2310/14* (2013.01); *C12N 2320/30* (2013.01); *C12Q 2600/158* (2013.01); *C12Q 2600/16* (2013.01); *G01N 2333/47* (2013.01)

(58) Field of Classification Search
None
See application file for complete search history.

(56) References Cited

FOREIGN PATENT DOCUMENTS

| WO | WO-2011/000894 A1 | 1/2011 | |
|---|---|---|---|
| WO | WO-2012/071513 A2 | 5/2012 | |
| WO | WO-2012/170979 A1 | 12/2012 | |
| WO | WO 2012170979 A1 * | 12/2012 | ......... A61K 31/7088 |

OTHER PUBLICATIONS

Thurner et al., 1999, JEM, vol. 190: 1669-1678.*
Wu et al., 2011, JCI, vol. 121: 2599-2613.*
Gao et al "VentX, a Novel Lymphoid-Enhancing Factor/T-Cell Factor-Associated Transcription Repressor, is a Putative Tumor Suppressor" Cancer Research vol. 70, pp. 202-211, 2010.
Park et al "IL-6 Regulates In Vivo Dendritic Cell Differentiation Through STAT3 Activation" Journal of Immunology vol. 173, pp. 3844-3854, 2004.

* cited by examiner

*Primary Examiner* — Amy E Juedes
(74) *Attorney, Agent, or Firm* — Cesari and McKenna, LLP

(57) ABSTRACT

The invention relates to human homeobox transcription factor VentX and its regulation of differentiation and maturation of human dendritic cells, and related therapeutic and diagnostic compositions and methods of use.

2 Claims, 17 Drawing Sheets

A.

B.

C.

D.

E.

F.

A.

B.

C.

D.

F.

GFP

GFP.VentX

A.

B.

C.

D.

E.

F.

G.

A.

B.

C.

D.

E.

F.

A.

Fluorescent Intensity -->
(FIG. 6B cont'd)

C.

D.

E.

F.

G.

HOMEOBOX TRANSCRIPTION FACTOR VENTX REGULATES DIFFERENTIATION AND MATURATION OF HUMAN DENDRITIC CELLS

PRIORITY CLAIMS AND RELATED APPLICATIONS

This application is the U.S. national phase of and claims priority to PCT/US14/33577, filed Apr. 10, 2014, which claims the benefit of priority from U.S. Provisional Application Ser. No. 61/810,610, filed on Apr. 10, 2013, the entire content of each of which is incorporated herein by reference in its entirety.

TECHNICAL FIELDS OF THE INVENTION

The invention generally relates to human biology discoveries and therapeutic and diagnostic compositions and methods based thereon. More particularly, the invention relates to human homeobox transcription factor VentX and its regulation of differentiation and maturation of human dendritic cells, and related therapeutic and diagnostic compositions and methods of use.

BACKGROUND OF THE INVENTION

Dendritic cells (DCs) are the most potent professional antigen-presenting cells that play critical roles in initiation of immune responses and maintenance of immune homeostasis. Derived from bone marrow hematopoietic stem/multipotent progenitor cells, DCs reside in an immature state in peripheral nonlymphoid tissues. (Geissmann, et al., 2010 Science 327(5966): p. 656-61; Liu, et al. 2010 Immunol Rev 234(1): p. 45-54.) These immature DCs are able of efficiently taking up and processing various antigens. Upon stimulation with inflammatory cytokines or microbial components, such as lipopolysaccharide (LPS) of bacteria, immature DCs undergo a maturation process and begin to migrate to local lymph nodes, where they interact with CD40 ligand on antigen specific T cells via CD40 and mature into potent immuno-stimulatory or immuno-tolerageneic cells (remove). (Geissmann, et al., 2010 Science 327(5966): p. 656-61; Randolph, et al. 2005 Nat Rev Immunol 5(8): p. 617-28; Mellman, et al. 2005 Adv Exp Med Biol 560: p. 63-7.) Maturation of DCs correlates with up-regulated expression of MHC class II and costimulatory molecules, production of immunostimulatory cytokines, and acquisition of capability to stimulate naive and antigen-specific T cells.

Intestinal mucosa is enriched with DCs, which reside in the lamina propria and regulate immune response to pathogen invasion. Maturation and function of intestinal DCs is regulated by both host factors and microbial components. Intestinal DCs detect the presence of pathogens through pattern recognition receptors, such as members of the toll-like receptor (TLR) family. Aberrant maturation and activation of intestinal DCs has been postulated to play a pathogenic role in auto-immune/inflammatory conditions, such as inflammatory bowel disease (IBD). It has been found that expression of TLR2, TLR4, CD40 is enhanced in DCs isolated from inflamed mucosa of IBD patients. Moreover, aberrant TLR signaling have been found to predispose patients to Crohn's disease. Evidence is accumulating, suggesting a potential role of targeting DCs in management of autoimmune-inflammatory conditions. However, currently, little is known about the intrinsic DC factors that can be manipulated to modulate DC maturation and functions.

Circulating monocytes derived DCs have been implicated in pathogenesis of inflammation, and the in vitro human monocytes derived dendritic cells have been widely used as a model system to explore the molecular mechanisms of DCs differentiation. Circulating monocytes derived DCs have been implicated in pathogenesis of inflammation. Previous studies showed that granulocyte-macrophage colony-stimulating factor (GM-CSF) and IL4 drive peripheral blood $CD14^+$ monocytes differentiation to $CD14^-CD1a^+$ DCs. Several cytokines such as IL6, IL10 and γ-IFN have been shown to negatively regulate the monocytes differentiation into DCs, whereas other cytokines are reported to promote DCs differentiation. (Chomarat, et al. 2000 Nat Immunol 1(6): p. 510-4; Mitani, et al. 2000 Br J Haematol 109(2): p. 288-95; Allavena, et al. 1998 Eur J Immunol 28(1): p. 359-69; Delneste, et al. 2003 Blood 101(1): p. 143-50; Chomarat, et al. 2003 J Immunol 171(5): p. 2262-9; Iwamoto, et al. 2007 J Immunol 179(3): p. 1449-57; Gabriele, et al. 2004 Blood 103(3): p. 980-7.) Recent gene profiling analysis has revealed a vast number of differentially expressed genes during induced human $CD14^+$ monocytes differentiation into DCs. (Le Naour, et al. 2001 J Biol Chem 276(21): p. 17920-31.) Nevertheless, the key transcriptional regulatory mechanisms underlying human monocytes to DCs differentiation remain poorly understood.

SUMMARY OF THE INVENTION

The invention is based, in part, on the discovery that that VentX is a key regulator of DC maturation and function and that VentX can serve as a target of intervention for inflammatory diseases and immune therapy.

VentX is a human homologue of the Xenopus homeobox gene Vent/Xom of the BMP4 signaling pathway, and was recently defined as a novel hematopoietic transcriptional factor controlling proliferation and differentiation of hematopoietic and immune cells. Initially identified as a novel LEF/TCF associated antagonist of the canonical Wnt signaling through reverse genetic modeling in Xenopus embryogenesis, VentX was found to be a transcriptional activator of the p53/p21 and $p16^{ink4a}$/Rb tumor suppression pathways. The critical role of VentX in hematopoietic cell development was further indicated by its role in controlling the proliferation and differentiation of both HSC/MPPs and monocyte to macrophage terminal differentiation.

As disclosed herein, it is shown that VentX is expressed in human primary DCs isolated from both peripheral blood as well as intestinal mucosa. Utilizing both loss- and gain-of-function approaches, it is demonstrated that VentX regulated DCs differentiation and maturation through an IL6 mediated mechanism. VentX expression is elevated in DCs isolated from inflamed mucosa of IBD patients and knockdown of VentX diminished the maturation response of DCs. Further, VentX is a downstream target and effecter of corticosteroid. The data disclosed herein demonstrates that VentX is a key regulator of DC maturation and function and that VentX can serve as a target of intervention for inflammatory diseases and immune therapy.

In one aspect, the invention generally relates to a method for regulating dendritic cells. The method includes administering to a subject in need thereof a therapeutically effective amount of a composition comprising an biological or chemical agent that exerts a modulating effect of human homeobox gene VentX.

In another aspect, the invention generally relates to a method for screening a compound for a regulatory function on dendritic cells. The method includes: (a) providing a cell comprising a polynuceotide comprising VentX promoter; (b) contacting the cell with a candidate compound; and (c) measuring the activity of VentX expression.

In yet another aspect, the invention generally relates to a pharmaceutical composition comprising a biological or chemical agent that exerts a regulatory effect on dendritic cells via a modulating effect of human homeobox gene VentX.

In yet another aspect, the invention generally relates to a method for diagnosing a subject for an inflammatory condition associated with maturation of dendritic cells, comprising detecting the expression profile of human homeobox gene VentX. In certain embodiments, the inflammatory condition is an autoimmnune disease.

In yet another aspect, the invention generally relates to a method for suppressing a tumor. The method includes administering to a subject in need thereof a therapeutically effective amount of a composition comprising an biological or chemical agent that exerts a modulating effect on dendritic cells function.

DEFINITIONS

Figure 1:
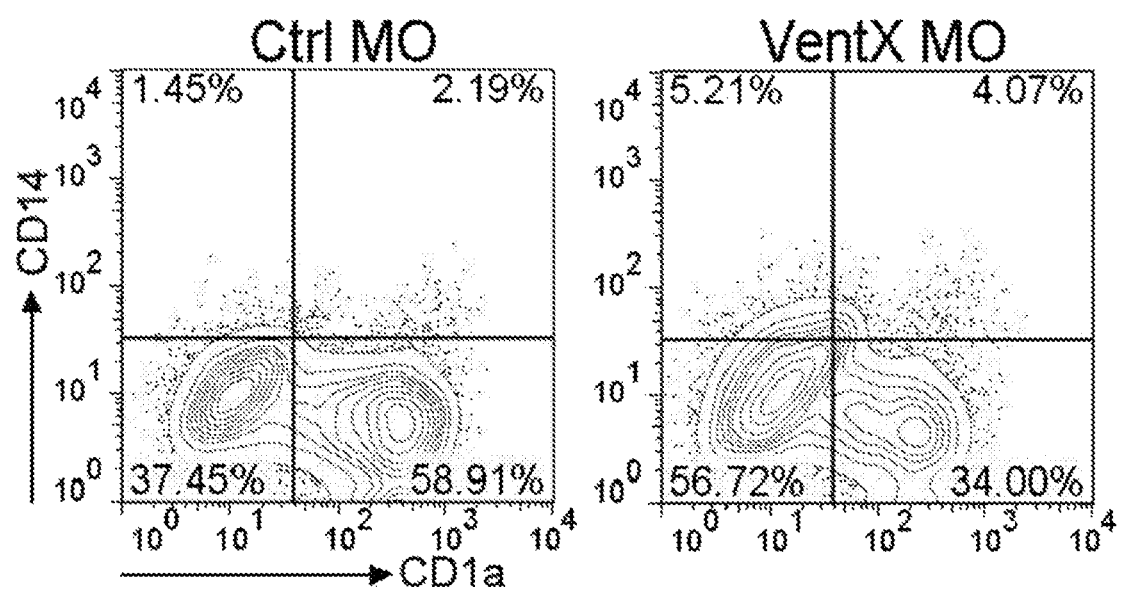
FIG. 1: VentX regulates primary monocyte to dendritic cell differentiation. (A) Human primary monocytes were transfected with morpholino (MO) oligonucleotides targeting VentX or the control MO as described in Materials and Methods. Twenty-four hours after transfection, GM-CSF and IL4 were added to culture medium to induce dendritic cells differentiation. Cells were harvested at 5 days after cytokines addition and the surface expression of CD1a and CD14 was analyzed by flow cytometry. (B) Bar graphs showed the percentage of $CD14^-CD1a^+$ cells from VentX MO or control MO transfected monocytes. The results were mean+standard deviation (SD) of six different experiments in (A). (C-D) Monocytes were transfected with VentX MO or control MO oligonucleotides as described above. The surface expression of CD1b and CD1c was analyzed by flow cytometry at 5 days after addition of cytokines. Results shown are representative of at least five separated experiments. (E) Monocytes were transfected with pcDNA-GFP or pcDNA-GFP.VentX plasmids through electroporation. Cytokines were added to culture medium 2 hours after transfection, and cells were harvested three days after cytokine addition for flow cytometry analysis. GFP positive population was gated for analysis of CD1a expression. (F) The mean+SD of four separated experiments in (E) was shown.
Figure 1:
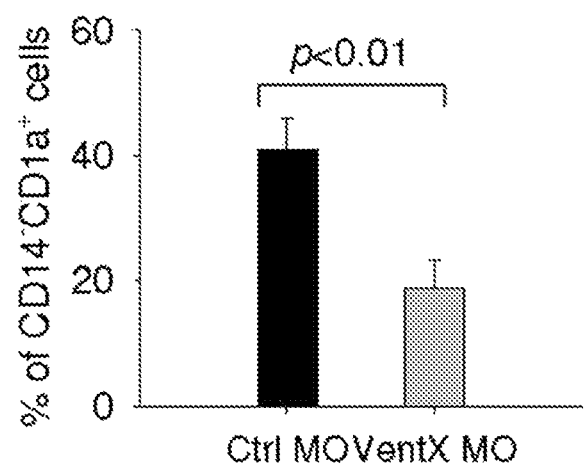
Figure 1:
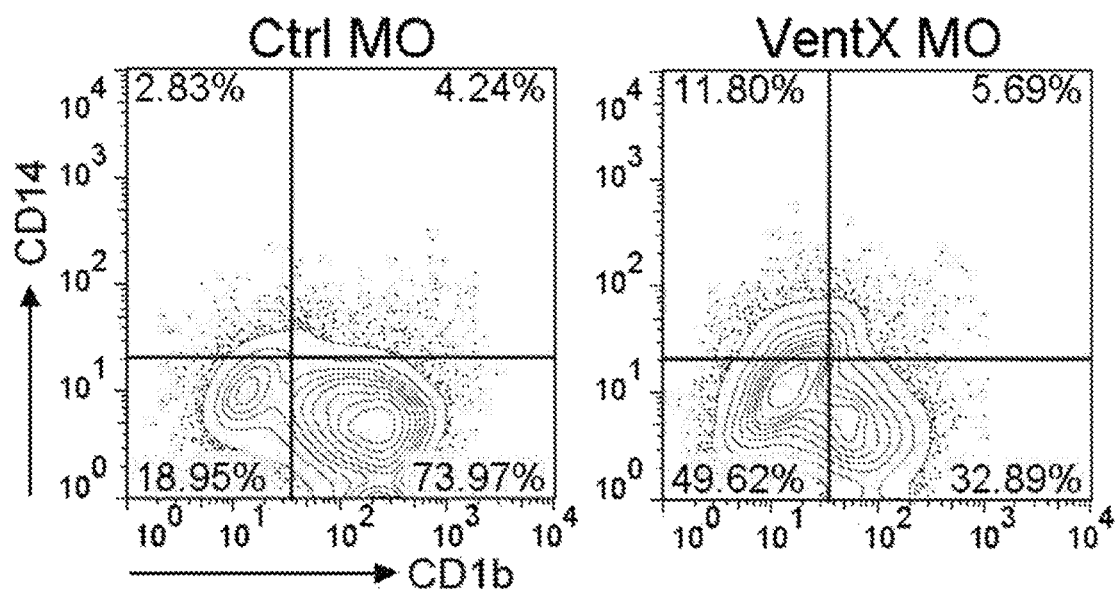
Figure 1:
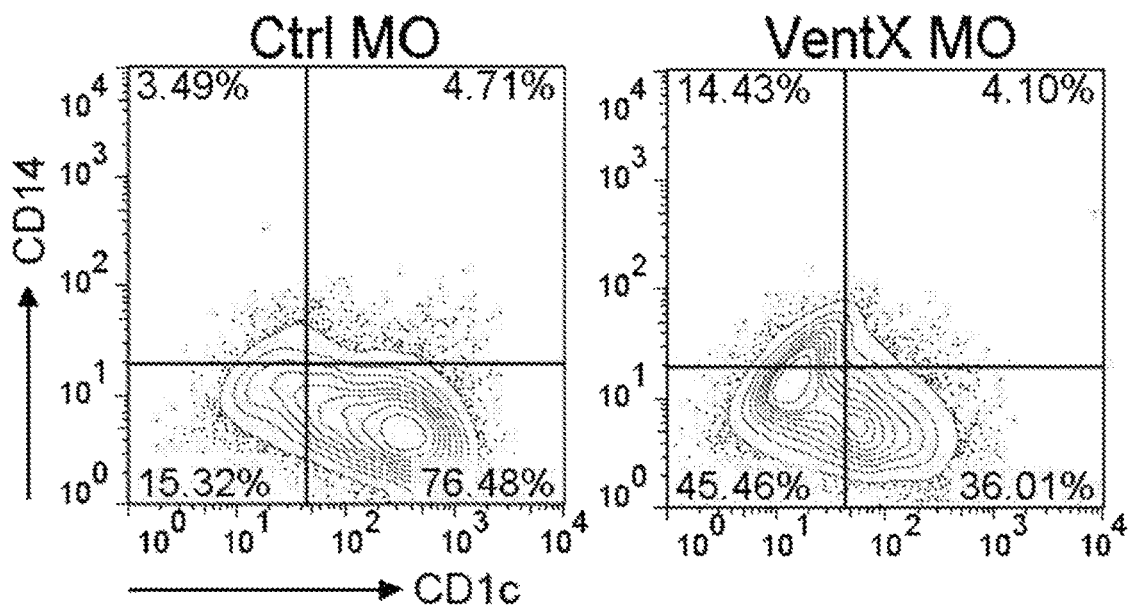
Figure 1:
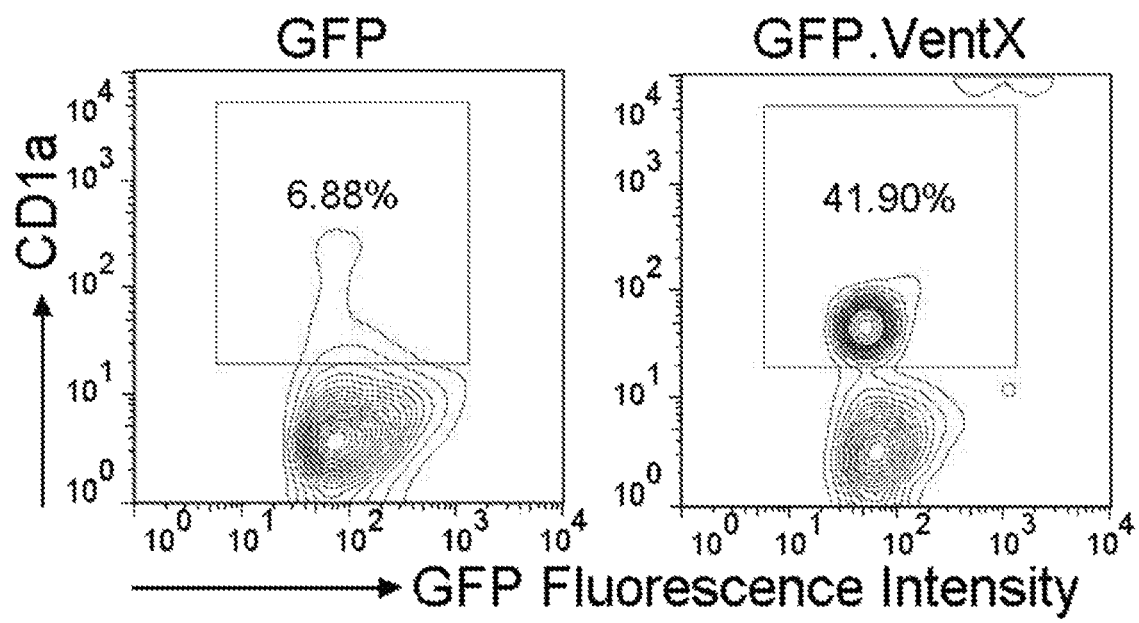
Figure 1:
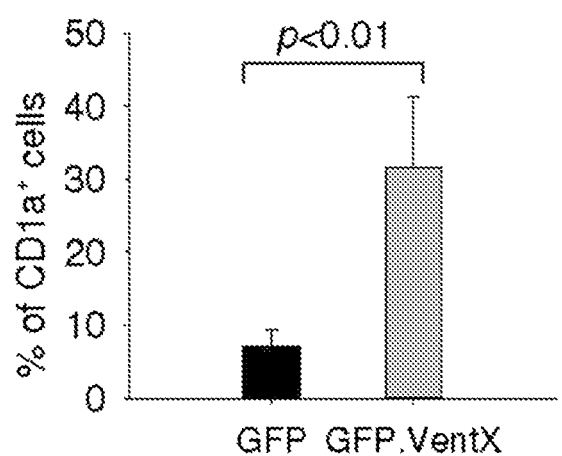

The definitions below are provided as summaries of concepts that are commonly understood by one of ordinary skill in the relevant art and are provided for the purposes of understanding of the subject matter disclosed herein. The definitions are not meant to be limitations of the invention or claims herein.

As used herein, the term "antibody" refers to molecules that are capable of binding an epitope or antigenic determinant. The term is meant to include whole antibodies and antigen-binding fragments thereof, including single-chain antibodies. The antibodies can be from any animal origin. Preferably, the antibodies are mammalian, e.g., human, murine, rabbit, goat, guinea pig, camel, horse and the like, or other suitable animals. Antibodies may recognize polypeptide or polynucleotide antigens. The term includes active fragments, including for example, an antigen binding fragment of an immunoglobulin, a variable and/or constant region of a heavy chain, a variable and/or constant region of a light chain, a complementarity determining region (cdr) and a framework region. The terms include polyclonal and monoclonal antibody preparations, as well as preparations including hybrid antibodies, altered antibodies, chimeric antibodies, hybrid antibody molecules, F(ab)$_2$ and F(ab) fragments; Fv molecules (for example, noncovalent heterodimers), dimeric and trimeric antibody fragment constructs; minibodies, humanized antibody molecules, and any functional fragments obtained from such molecules, wherein such fragments retain specific binding.

The use of the singular terms "a" or "an" or "the" antibody are not meant to be limited to a single antibody when it is clear that more than one antibody is present in the composition or preparation. In addition, unless indicated otherwise, the singular term for "antibody" may include a collection of antibodies that are not necessarily heterogenous in their structures or specificities.

As used herein, the term "humanized" antibodies refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (e.g., a humanized mouse antibody which contains all six CDRs from the mouse antibodies). Other forms of humanized antibodies have one or more CDRs (one, two, three, four, five, six) that are altered with respect to the original antibody.

The term "binds specifically," in the context of antibody binding, refers to high avidity and/or high affinity binding of an antibody to a specific epitope. Hence, an antibody that binds specifically to one epitope (a "first epitope") and not to another (a "second epitope") is a "specific antibody." An antibody specific to a first epitope may cross react with and bind to a second epitope if the two epitopes share homology or other similarity. The term "binds specifically," in the context of a polynucleotide, refers to hybridization under stringent conditions. Conditions that increase stringency of both DNA/DNA and DNA/RNA hybridization reactions are widely known and published in the art (Curr. Prot. Molec. Biol., John Wiley & Sons (2001)).

As used herein, the term "antigen" refers to a molecule capable of being bound by an antibody. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and/or T-cell epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

As used herein, the term "epitope" refers to basic element or smallest unit of recognition by an individual antibody or T-cell receptor, and thus the particular domain, region or molecular structure to which said antibody or T-cell receptor binds. An antigen may consist of numerous epitopes while a hapten, typically, may possess few epitopes.

As used herein, the term "nucleic acid molecule," "nucleotide," "oligonucleotide," "polynucleotide," and "nucleic acid" are used interchangeably herein to refer to polymeric forms of nucleotides of any length. They can include both double- and single-stranded sequences and include, but are not limited to, cDNA from viral, prokaryotic, and eukaryotic sources; mRNA; genomic DNA sequences from viral (e.g., DNA viruses and retroviruses) or prokaryotic sources; RNAi; cRNA; antisense molecules; ribozymes; and synthetic DNA sequences. The term also captures sequences that include any of the known base analogs of DNA and RNA.

As used herein, a "complementary" nucleotide sequence acid molecule is a one that is comprised of its base pair complements. Deoxyribonucleotides with the base adenine are complementary to those with the base thymidine, and deoxyribonucleotides with the base thymidine are complementary to those with the base adenine. Deoxyribonucleotides with the base cytosine are complementary to those with the base guanine, and deoxyribonucleotides with the base guanine are complementary to those with the base cytosine. Ribonucleotides with the base adenine are complementary to those with the base uracil, and deoxyribonucleotides with the base uracil are complementary to those with the base adenine. Ribonucleotides with the base cytosine are complementary to those with the base guanine, and deoxyribonucleotides with the base guanine are complementary to those with the base cytosine.

As used herein, the term "promoter" refers to a DNA regulatory region capable of binding RNA polymerase in a mammalian cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence may be a transcription initiation site, as well as protein binding domains (consensus sequences) responsible for the binding of RNA polymerase. Eukaryotic promoters will often, but not always, contain "TATA" boxes and "CAT" boxes. Promoters include those that are naturally contiguous to a nucleic acid molecule and those that are not naturally contiguous to a nucleic acid molecule. Additionally, the term "promoter" includes inducible promoters, conditionally active promoters such as a cre-lox promoter, constitutive promoters, and tissue specific promoters.

As used herein, the term "transfected" means possessing introduced DNA or RNA, with or without the use of any accompanying facilitating agents such as lipofectamine. Methods for transfection that are known in the art include calcium phosphate transfection, DEAE dextran transfection, protoplast fusion, electroporation, and lipofection.

As used herein, the term "expression of a nucleic acid molecule" refers to the conversion of the information contained in the nucleic acid molecule into a gene product. The gene product can be the direct transcriptional product of a gene (e.g., mRNA, tRNA, rRNA, antisense RNA, ribozyme, structural RNA, or any other type of RNA) or a peptide or polypeptide produced by translation of an mRNA. Gene products also include RNAs that are modified by processes such as capping, polyadenylation, methylation, and editing; and proteins modified by, for example, methylation, acetylation, phosphorylation, ubiquitination, ADP-ribosylation, myristilation, and glycosylation.

As used herein, the term "host cell" refers to an individual cell or a cell culture that can be or has been a recipient of any recombinant vector(s) or isolated polynucleotide(s). Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell that comprises a recombinant vector of the invention may be called a "recombinant host cell."

As used herein, the term an "isolated" or "substantially isolated" molecule (such as a polypeptide or polynucleotide) is one that has been manipulated to exist in a higher concentration than in nature or has been removed from its native environment. For example, a subject antibody is isolated, purified, substantially isolated, or substantially purified when at least 10%, or 20%, or 40%, or 50%, or 70%, or 90% of non-subject-antibody materials with which it is associated in nature have been removed. For example, a polynucleotide or a polypeptide naturally present in a living animal is not "isolated," but the same polynucleotide or polypeptide separated from the coexisting materials of its natural state is "isolated." Further, recombinant DNA molecules contained in a vector are considered isolated for the purposes of the present invention. Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Thus, not all "isolated" molecules need be "purified."

As used herein, the term "purified" when used in reference to a molecule, it means that the concentration of the molecule being purified has been increased relative to molecules associated with it in its natural environment, or environment in which it was produced, found or synthesized. Naturally associated molecules include proteins, nucleic acids, lipids and sugars but generally do not include water, buffers, and reagents added to maintain the integrity or facilitate the purification of the molecule being purified. According to this definition, a substance may be 5% or more, 10% or more, 20% or more, 30% or more, 40% or more, 50% or more, 60% or more, 70% or more, 80% or more, 90% or more, 95% or more, 98% or more, 99% or more, or 100% pure when considered relative to its contaminants.

As used herein, the term "biologically active" entity, or an entity having "biological activity," is one having structural, regulatory, or biochemical functions of a naturally occurring molecule or any function related to or associated with a metabolic or physiological process. Biologically active polynucleotide fragments are those exhibiting activity similar, but not necessarily identical, to an activity of a polynucleotide of the present invention. The biological activity can include an improved desired activity, or a decreased undesirable activity. For example, an entity demonstrates biological activity when it participates in a molecular interaction with another molecule, such as hybridization, when it has therapeutic value in alleviating a disease condition, when it has prophylactic value in inducing an immune response, when it has diagnostic and/or prognostic value in determining the presence of a molecule, such as a biologically active fragment of a polynucleotide that can, for example, be detected as unique for the polynucleotide molecule, or that can be used as a primer in a polymerase chain reaction. A biologically active polypeptide or fragment thereof includes one that can participate in a biological reaction.

As used herein, the terms "subject," "individual," and "patient" are used interchangeably herein to refer to a living animal, including a human and a non-human animal. The subject may, for example, be an organism possessing immune cells capable of responding to antigenic stimulation, and stimulatory and inhibitory signal transduction through cell surface receptor binding. The subject may be a mammal, such as a human or non-human mammal, for example, dogs, cats, pigs, cows, sheep, goats, horses, rats, and mice. The term "subject" does not preclude individuals that are entirely normal with respect to a disease, or normal in all respects.

As used herein, a "patient sample" is any biological specimen derived from a patient. The term includes, but is not limited to, biological fluids such as blood, serum, plasma, urine, cerebrospinal fluid, tears, saliva, lymph, dialysis fluid, lavage fluid, semen, and other liquid samples, as well as cell and tissues of biological origin. The term also includes cells or cells derived therefrom and the progeny thereof, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. This definition encompasses samples that have been manipulated in any way after their procurement, such as by treatment with reagents, solubilization, or enrichment for certain components, such as polynucleotides or polypeptides. Also included in the term are derivatives and fractions of patient samples. A patient sample may be used in a diagnostic, prognostic, or other monitoring assay.

As used herein, the term "modulate" refers to the production, either directly or indirectly, of an increase or a decrease, a stimulation, inhibition, interference, or blockage in a measured activity when compared to a suitable control. A "modulator" of a polypeptide or polynucleotide or an "agent" are terms used interchangeably herein to refer to a substance that affects, for example, increases, decreases, stimulates, inhibits, interferes with, or blocks a measured activity of the polypeptide or polynucleotide, when compared to a suitable control.

As used herein, the terms "disease" or "disorder" refer to a pathological condition, for example, one that can be identified by symptoms or other identifying factors as diverging from a healthy or a normal state. The term "disease" includes disorders, syndromes, conditions, and injuries. Diseases include, but are not limited to, proliferative, inflammatory, immune, metabolic, infectious, and ischemic diseases.

As used herein, the term "inflammatory condition(s)" refers to the group of conditions including, rheumatoid arthritis, osteoarthritis, juvenile idiopathic arthritis, psoriasis, allergic airway disease (e.g., asthma, rhinitis), inflammatory bowel diseases (e.g., Crohn's disease, colitis), endotoxin-driven disease states (e.g., complications after bypass surgery or chronic endotoxin states contributing to e.g. chronic cardiac failure), and related diseases involving cartilage, such as that of the joints. Partcicularly the term refers to rheumatoid arthritis, osteoarthritis, allergic airway disease (e.g., asthma) and inflammatory bowel diseases.

As used herein, the term "autoimmune disease(s)" refers to the group of diseases including obstructive airways disease, including conditions such as COPD, asthma (e.g., intrinsic asthma, extrinsic asthma, dust asthma, infantily asthma) particularly chronic or inveterate asthma (for example late asthma and airway hyperreponsiveness), bronchitis, including bronchial asthma, systemic lupus erythematosus (SLE), multiple sclerosis, type I diabetes mellitus and complications associated therewith, atopic eczema (atopic dermatitis), contact dermatitis and further eczematous dermatitis, inflammatory bowel disease (e.g., Crohn's disease and ulcerative colitis), atherosclerosis and amyotrophic lateral sclerosis. Particularly the term refers to COPD, asthma, systemic lupus erythematosis, type I diabetes mellitus and inflammatory bowel disease.

As used herein the term "proliferative disease(s)" refers to conditions such as cancer (e.g., uterine leiomyosarcoma or prostate cancer), myeloproliferative disorders (e.g., polycythemia vera, essential thrombocytosis and myelofibrosis), leukemia (e.g., acute myeloid leukaemia and acute lymphoblastic leukemia), multiple myeloma, psoriasis, restenosis, sclerodermitis or fibrosis. In particular the term refers to cancer, leukemia, multiple myeloma and psoriasis.

As used herein, the terms "cancer" and "cancerous" refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer.

As used herein, the term "tumor" refers to any malignant or neoplastic cell.

As used herein, the term "treatment" covers either prophylactic and/or therapeutic treatments including any administration or application of remedies for disease in a mammal, including a human, and includes inhibiting the disease. It includes arresting disease development and relieving the disease, such as by causing regression or restoring or repairing a lost, missing, or defective function, or stimulating an inefficient process. As used herein, the term "preventing" includes providing prophylaxis with respect to the occurrence or recurrence of a disease in a subject that may be predisposed to the disease but has not yet been diagnosed with the disease. Treatment and prophylaxis can be administered to an organism, including a human, or to a cell in vivo, in vitro, or ex vivo, and the cell subsequently administered the subject.

As used herein, the term "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount." The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

As used herein, the term "carrier" refers to a solid, semisolid or liquid filler, diluent, encapsulating material, formulation auxiliary, or excipient of any conventional type. A "pharmaceutically acceptable carrier" refers to a non-toxic "carrier." A pharmaceutically acceptable carrier is non-toxic to recipients at the dosages and concentrations employed and is compatible with other ingredients of the formulation. Pharmaceutically acceptable carriers can be, for example, vehicles, adjuvants, or diluents.

As used herein, the terms "polypeptide" and "protein" are used interchangeably to refer to a polymer of amino acid residues, and are not limited to a minimum length. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation, and the like. Furthermore, a "polypeptide" may refer to a protein which includes modifications, such as deletions, additions, and substitutions (generally conservative in nature), to the native sequence, as long as the protein maintains the desired activity. These modifications may be deliberate or may be accidental.

As used herein, the term "receptor" refers to proteins or glycoproteins or fragments thereof capable of interacting with another molecule, called the ligand. The ligand may belong to any class of biochemical or chemical compounds. The ligand is usually an extracellular molecule which, upon binding to the receptor, usually initiates a cellular response, such as initiation of a signal transduction pathway. The receptor need not necessarily be a membrane-bound protein.

As used herein, the term "recombinant," with respect to a nucleic acid molecule, means a polynucleotide of genomic, cDNA, viral, semisynthetic, and/or synthetic origin which, by virtue of its origin or manipulation, is not associated with all or a portion of the polynucleotide with which it is associated in nature. The term "recombinant", as used with respect to a protein or polypeptide, means a polypeptide produced by expression of a recombinant polynucleotide. The term "recombinant" as used with respect to a host cell means a host cell into which a recombinant polynucleotide has been introduced.

As used herein, the phrase "recombinant virus" refers to a virus that is genetically modified by the hand of man. The phrase covers any virus known in the art.

As used herein, the term "vector" refers to an agent (e.g., a plasmid or virus) used to transmit genetic material to a host cell or organism. A vector may be composed of either DNA or RNA.

As used herein, the term "interfering RNA" or "RNAi" or "interfering RNA sequence" refers to double-stranded RNA (i.e., duplex RNA) that is capable of reducing or inhibiting expression of a target gene (i.e., by mediating the degradation of mRNAs which are complementary to the sequence of the interfering RNA) when the interfering RNA is in the same cell as the target gene. Interfering RNA thus refers to the double-stranded RNA formed by two complementary strands or by a single, self-complementary strand. Interfering RNA may have substantial or complete identity to the target gene or may comprise a region of mismatch (i.e., a mismatch motif). The sequence of the interfering RNA can correspond to the full length target gene, or a subsequence thereof. Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length).

As used herein, the term "sample" refers to a sample from a human, animal, or to a research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

DETAILED DESCRIPTION OF THE INVENTION

The invention is based, in part, on the discovery that VentX plays an essential role in regulation of DC maturation and function. VentX regulates DCs differentiation and maturation through an IL6 mediated mechanism. VentX expression is elevated in DCs isolated from inflamed mucosa of IBD patients and knockdown of VentX diminished the maturation response of DCs. The data disclosed herein demonstrates that VentX can serve as a target of intervention for inflammatory diseases and immune therapy.

The disclosure herein establishes that ablation of VentX expression in monocytes significantly impairs their differentiation into DCs. Conversely, overexpression of VentX in monocytic cells THP1 accelerates their differentiation towards DCs. Increased IL6 expression partially accounted for the DCs differentiation defects in monocytes with VentX knockdown. Clinically important is the finding that VentX expression was elevated in intestinal lamina propria DCs (LPDCs) from inflamed mucosa of inflammatory bowel diseases patients. Knockdown experiments showed that VentX is essential for the maturation of LPDCs. In addition, steroids treatments markedly lowered VentX expression in LPDCs and enforced expression of VentX counteracted the effects of steroid. In conclusion, the data disclosed herein demonstrates that VentX is a critical transcriptional regulator of DC differentiation and maturation, and a potential interventional target of immune regulation and therapy.

The mechanism of DCs differentiation and maturation is the focus of great interests for its potential application in immune regulation and therapy. While a wealth of information has been learned about the cytokines that affect monocytes differentiation into DCs, the key transcriptional regulatory events underlying DC differentiation remained to be fully defined. (Gabriele, et al. 2004 Blood 103(3): p. 980-7; Hart, et al. 2005 Gastroenterology 129(1): p. 50-65; Dillon, et al. 2010 J Immunol 184(12): p. 6612-21; Bell, et al. 2001 J Immunol 166(8): p. 4958-67.) In the present study, it was shown that the human homeobox protein VentX is a key regulator of DC differentiation and maturation. Evidence was provided showing that VentX expression is elevated in DCs isolated from inflamed mucosa of IBD patients. It was found that VentX is a downstream target of the corticosteroid commonly used for treating autoimmune-inflammatory conditions.

Recent studies indicated that VentX is a key hematopoietic transcriptional factor whose expression is restricted and highly regulated during ontogenesis of all lineages of hematopoietic cells. It was found that VentX governs proliferation and differentiation of hematopoietic cells during both early hematopoiesis and terminal differentiation and maturation. Mechanistically, VentX was found to antagonize the canonical Wnt signaling and activate p53/p21 and pRb/p16 senescence pathways to exert its effects on cell proliferation. Meanwhile, VentX activates a variety of cell differentiation signaling during lineage differentiation of hematopoietic cells. Knockdown VentX blocks differentiation of hematopoietic cells during both early stage as well as terminal stage, suggesting that VentX is a general permissive factor for the differentiation of hematopoietic cells. Whether VentX plays a role in linage development remains to be further defined. Results showed that ectopic expression of VentX in U937 cell promotes macrophage development, whereas ectopic expression of VentX in THP1 cell promote DC development, suggesting that the effects of VentX on differentiation of hematopoietic cells are cell-type specific.

Figure 3:
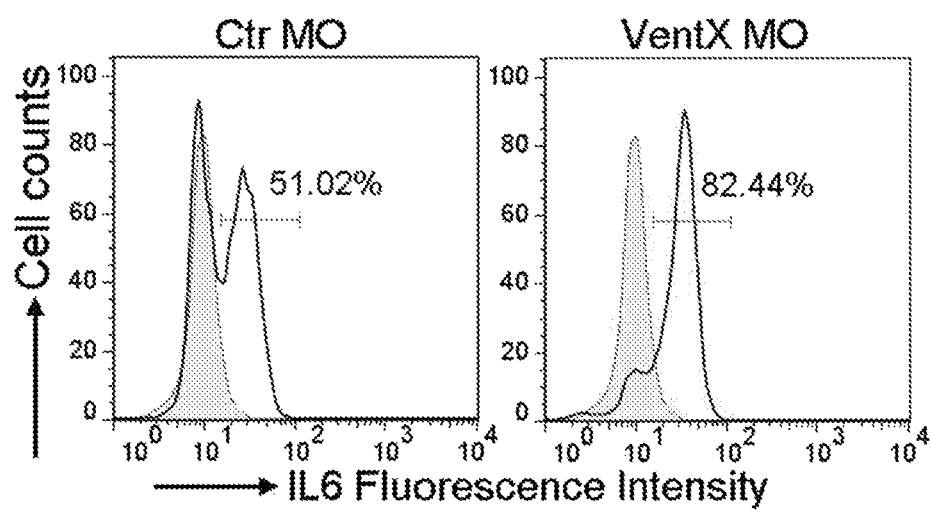
FIG. 3: VentX suppresses IL6 expression. (A) Monocytes were transfected with VentX MO or control MO and GM-CSF and IL4 were added into culture medium for five days. Intracellular IL6 level was determined by flow cytometry. (B) Monocyte was transfected with pcDNA-GFP or pcDNA-GFP.VentX through electroporation. Cells were then cultured in the presence of GM-CSF and IL4 for three days. Intracellular staining of IL6 was performed in transfected cells and IL6 level in GFP positive cells was analyzed by flow cytometry. Results shown are one representative of at least three separated experiments. (C) Monocytes were transfected and harvested as described above. Real-time PCR was performed to determine the mRNA level of IL6. (D) The −592 by human IL6 promoter reporter was transfected with pcDNA-GFP or pcDNA-VentX plasmid into primary monocytes through electroporation. Two days after transfection, cells were harvested to analyze the luciferase activity. (E) Various IL6 promoter reporters were transfected into U2OS cells that express VentX upon induction with doxycycline. Cells were harvested at 2 days after DOX addition and luciferase activity in the presence or absence of DOX was analyzed. (F) The −80 by IL6 promoter reporter with mutant NFκB binding site was transfected into U2OS cells. Then DOX was added into medium or omitted, and luciferase activity was determined at two days after transfection. (G) THP1 cells expressing GFP or GFP.VentX were treated with DOX for 2 days and harvested for ChIP assay with anti-NFκB/p65 antibody. Human IL6 promoter region containing an NFκB binding site was amplified by real-time PCR as described in Materials and Methods. Results shown are M+SD of triplicates from one representative experiment and three independent experiments were performed.
Figure 3:
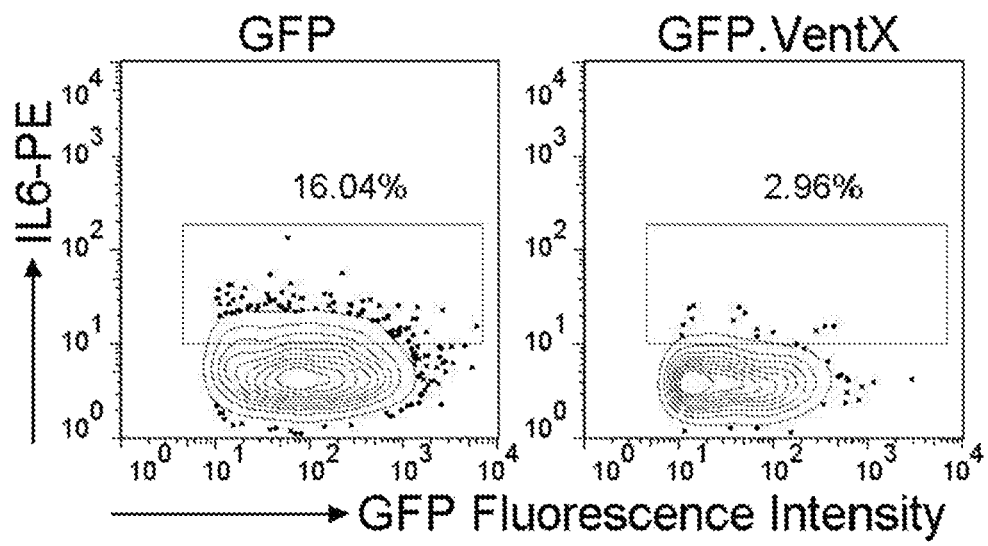
Figure 3:
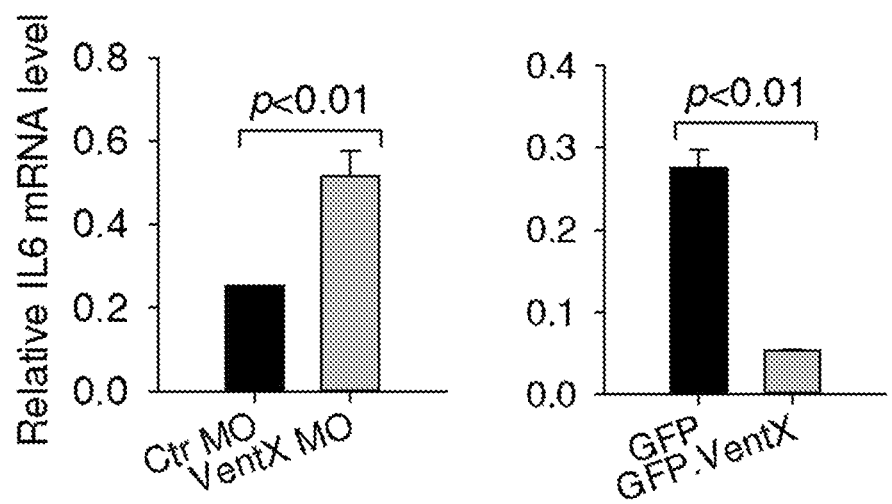
Figure 3:
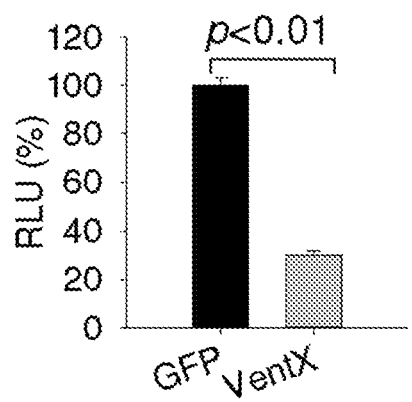
Figure 3:
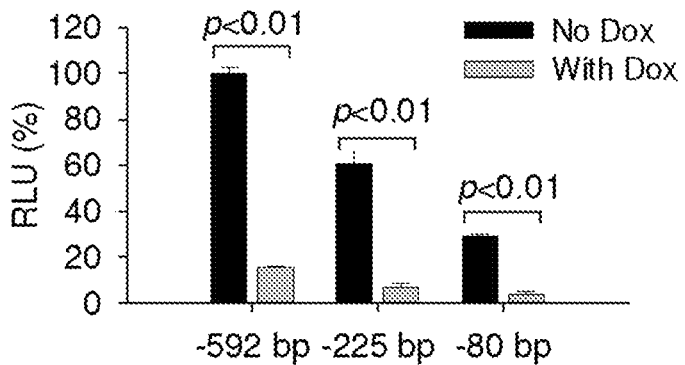
Figure 3:
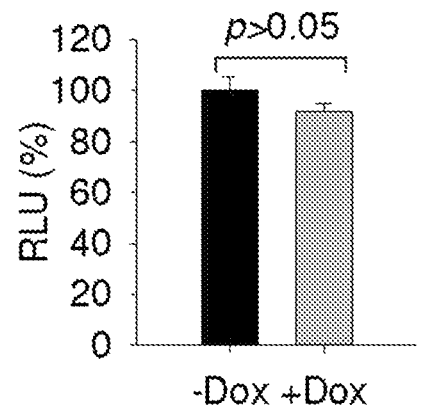
Figure 3:
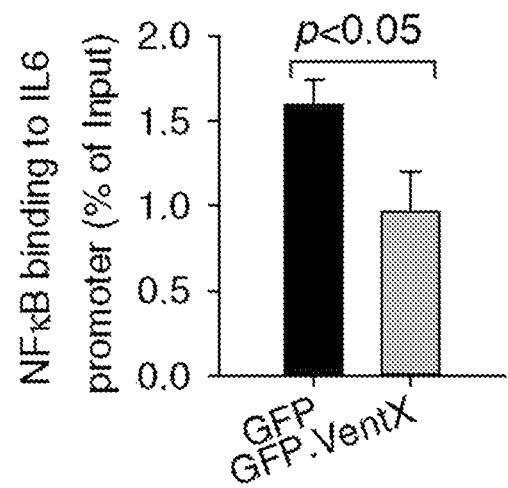

The exploration of the mechanisms underlying VentX regulated DCs differentiation led to IL6, a critical signal involved in DC differentiation. (Chomarat, et al. 2000 Nat Immunol 1(6): p. 510-4; Mitani, et al. 2000 Br J Haematol 109(2): p. 288-95; Park, et al. 2004 J Immunol 173(6): p. 3844-54.) Prior studies showed that inhibition of DCs differentiation by γ-IFN, Wnt5a, HLA-G and transcription factor ESE-3 led to increased IL6 secretion or signaling [9, 35-38]. (Delneste, et al. 2003 Blood 101(1): p. 143-50; Liang, et al. 2008 Proc Natl Acad Sci USA 105(24): p. 8357-62; Appel, et al. 2006 Blood 107(8): p. 3265-70; Valencia, et al. 2011 J Immunol 187(8): p. 4129-39; Bharadwaj, et al. 2007 Cancer Res 67(11): p. 5479-88.) Results showed that IL6 expression was increased in DCs with VentX knockdown (FIGS. 3A and C), whereas overexpression of VentX inhibited IL6 expression (FIGS. 3B and C). Importantly, it was found that impaired DC differentiation upon VentX knockdown can be partially rescued by diminishing IL6 signaling with IL6 antibody. Mechanistic exploration suggested that VentX regulates IL6 expression in part through its effects on the NFκB binding to IL6 promoter region in THP1 cells. Consistent with cell type specific effects of VentX on differentiation, previous studies showed that VentX promotes IL expression in macrophage U937 cells. The mechanisms underlying the cell type specific effects of VentX-regulated IL6 expression is of great interest and a target of current investigation.

Recent advance in DC biology suggested that aberrant maturation and activation of circulating monocyte is involved in pathogenesis of intestinal mucosa inflammation. The findings that VentX expression is aberrantly elevated in DC cells isolated from inflamed mucosa of IBD patients suggested the clinical relevance of the identification of VentX as a novel key regulator of DC differentiation and maturation. The potential application of targeting VentX in modulating DC activities and autoimmune/inflammatory conditions has been indicated by the findings that VentX is a downstream target of corticosteroid and that VentX mediates inhibitory effects of steroid on DC maturation and activation. Further studies are needed to define how VentX-regulated DC differentiation and activation are modulated by host and microbial factors. Such information would be critical for understanding regionalized damage of intestinal mucosa in IBD. Refractory of corticosteroid and other currently available immunosuppressants are the central issues of managing autoimmune and inflammatory diseases.

In one aspect, the invention generally relates to a method for regulating dendritic cells. The method includes administering to a subject in need thereof a therapeutically effective amount of a composition comprising an biological or chemical agent that exerts a modulating effect of human homeobox gene VentX.

In certain embodiments, regulating dendritic cells comprises affecting a maturation response of dendritic cells.

In certain embodiments, the biological or chemical agent that exerts an inhibitory effect of human homeobox gene VentX.

In certain embodiments, the biological or chemical agent is a polypeptide.

In certain embodiments, the biological or chemical agent comprises a VentX mutant lacking the homeodomain as a blocking polypeptide.

In certain embodiments, the biological or chemical agent is an antibody fragment.

In certain embodiments, the biological or chemical agent is an oligonucleotide. In certain embodiments, the oligonucleotide is an RNAi.

In another aspect, the invention generally relates to a method for screening a compound for a regulatory function on dendritic cells. The method includes: (a) providing a cell comprising a polynuceotide comprising VentX promoter; (b) contacting the cell with a candidate compound; and (c) measuring the activity of VentX expression.

In certain embodiments, the candidate compound is a small molecule agent.

In certain embodiments, the candidate compound is a polypeptide.

In certain embodiments, the candidate compound is an oligonucleotide.

In yet another aspect, the invention generally relates to a pharmaceutical composition comprising a biological or chemical agent that exerts a regulatory effect on dendritic cells via a modulating effect of human homeobox gene VentX.

In certain embodiments of the pharmaceutical composition, the modulating effect comprises an inhibiting effect relevant in treatment of an inflammatory condition.

In certain embodiments of the pharmaceutical composition, the inflammatory condition is an autoimmnune disease.

In certain embodiments of the pharmaceutical composition, the biological or chemical agent is a polypeptide.

In certain embodiments of the pharmaceutical composition, the biological or chemical agent is an antibody.

In certain embodiments of the pharmaceutical composition, the biological or chemical agent is an oligonucleotide.

In yet another aspect, the invention generally relates to a method for diagnosing a subject for an inflammatory condition associated with maturation of dendritic cells, comprising detecting the expression profile of human homeobox gene VentX. In certain embodiments, the inflammatory condition is an autoimmnune disease.

In yet another aspect, the invention generally relates to a method for suppressing a tumor. The method includes administering to a subject in need thereof a therapeutically effective amount of a composition comprising an biological or chemical agent that exerts a modulating effect on dendritic cells function.

In certain embodiments, the modulating effect on dendritic cells function comprises a modulating effect via human homeobox gene VentX (e.g., enhancing DC function by increasing VentX via either induced or direct transfect into the DC cells. In certain embodiments, the biological or chemical agent is a polypeptide. In certain embodiments, the biological or chemical agent is an antibody fragment. In certain embodiments, the biological or chemical agent is an oligonucleotide. In certain embodiments, the oligonucleotide is an RNAi.

VentX Regulates Primary Monocytes to Dendritic Cells Differentiation

Following a recent finding that VentX is expressed in human primary monocytes, VentX expression was examined during primary monocytes to dendritic cells differentiation induced by GM-CSF and IL-4 treatment. (Grassl, et al. 1999 *J Am Soc Nephrol* 10(7): p. 1466-77.) It was found that VentX expression underwent a marked increase at both mRNA and protein levels during the induced DC differentiation. To explore potential role of VentX in DC differentiation, the effects of VentX knockdown on in vitro DCs differentiation were examined. VentX siRNA produced marginal VentX knockdown efficiency in monocytes after 5 days of transfection (unpublished data), whereas differentiation of DCs from monocytes in vitro requires 5-7 days of incubation with GM-CSF and IL4. (Iwamoto, et al. 2007 *J Immunol* 179(3): p. 1449-57; Gabriele, et al. 2004 *Blood* 103(3): p. 980-7.) To obtain a long-lasting knockdown effect of VentX in monocytes, a morpholino (MO) mediated VentX knockdown strategy was developed. Two different morpholino antisense oligonucleotides were designed (VentX MO and VentX MO-2) and tested for the knockdown efficiency of VentX. Both morpholino sequences inhibited VentX expression in DCs compared with control sequence at 5 days after transfection. Freshly isolated $CD14^+CD1a^-$ monocytes differentiate in vitro into immature $CD14^-CD1a^+$ DCs when cultured with GM-CSF and IL-4. (Bell, et al. 2001 *J Immunol* 166(8): p. 4958-67.) Surface expression of CD1a antigen was examined in monocytes transfected with control MO or VentX MO respectively. As shown in FIG. 1, transfection of VentX MO MO led to a substantial reduction in the percentage of $CD14^-CD1a$ cells (FIG. 1 A-B) in comparison with the control MO. The surface expression of CD1b, CD1c and CD11c, which are considered as additional differentiation markers of monocytes-derived DCs, were similarly downregulated in VentX MO transfected cells. (Osugi, et al. 2002 *Blood* 100(8): p. 2858-66.) Transfection of VentX MO did not cause excess cell death in DCs (data not shown), which ruled out the possibility that the decreased differentiation was due to compromised cell viability. The expression of other surface antigens such as CD16, CD36 and CD64, mannose receptor (MR) and Toll-like receptor 4 (TLR4) delete remained unchanged in VentX MO transfected DCs, further supporting that VentX MO transfection exerted specific effects on DC differentiation. To corroborate the role of VentX in regulating DCs differentiation, VentX was ectopically expressed in primary monocytes and the CD14$^-$CD1a$^+$ cells were determined after 3 days of cytokines treatment. Overexpression of VentX in monocytes greatly accelerated the DCs differentiation (FIG. 1E-F). Taken together, these data demonstrated that VentX is a critical regulator of primary monocytes to DCs differentiation.

VentX Promotes Dendritic Cells Differentiation

Figure 2:
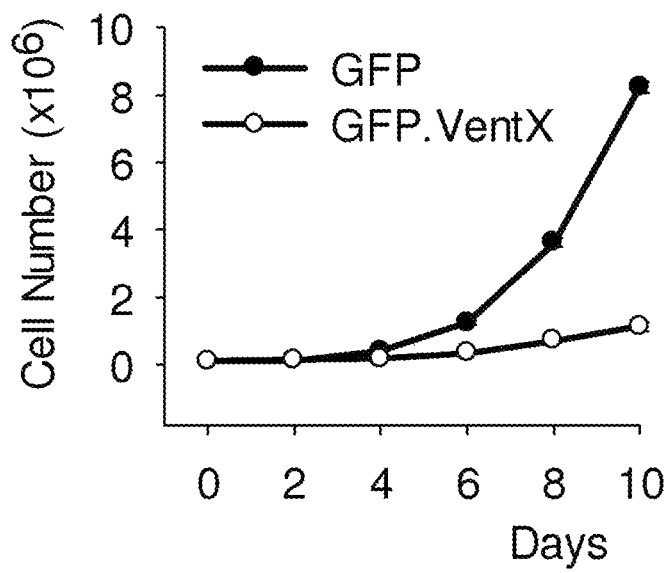
FIG. 2: VentX overexpression promotes THP1 cells differentiation towards dendritic cells. (A) THP1 cell lines expressing GFP or GFP.VentX under the control of tetracycline-inducible promoter were treated with 1.0 μg/mL doxycycline (DOX) for ten days. Cell numbers at indicated days were counted and plotted. (B) Cell cycle profiles of THP1 cells expressing GFP or GFP.VentX after ten days exposure to DOX. Cells were stained with propidium iodide and analyzed by flow cytometry. (C-D) THP1 cells were treated with DOX for 3 days and harvested. The mRNA RNA level (C) and protein level (D) of p21 and c-myc were analyzed by real-time PCR and western blot, respectively. (E-F) THP1 cells were treated with DOX and cultured under conditions described in Materials and Methods to induce dendritic cells differentiation. (E) At two days after treatment, cells were harvested to analyze the surface expression of indicated antigens by flow cytometry. (F) Cells were photographed using phase contrast microscopy to show the morphological changes of VentX expressing cells. Results shown are representative of at least three separated experiments.
Figure 2:
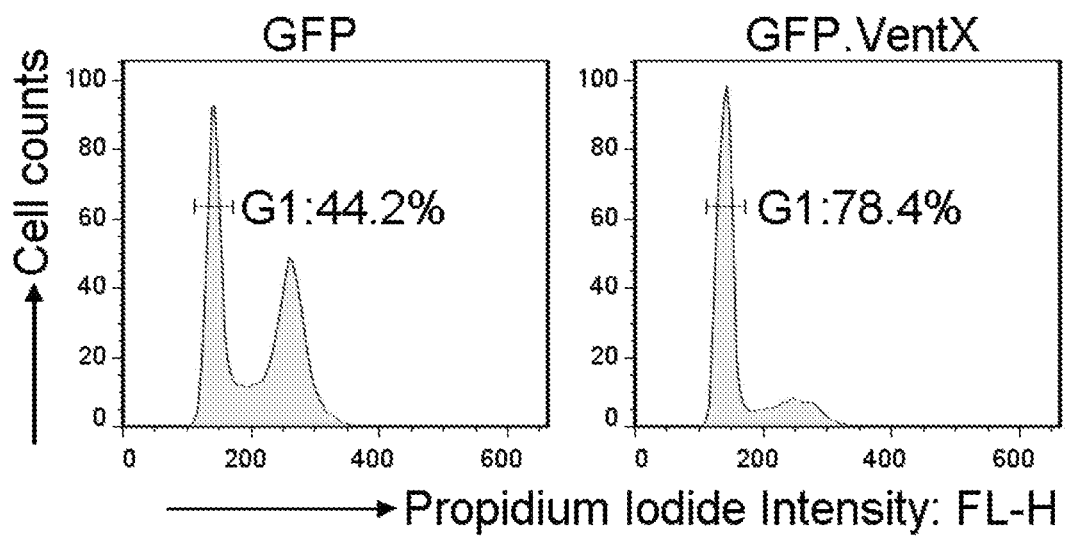
Figure 2:
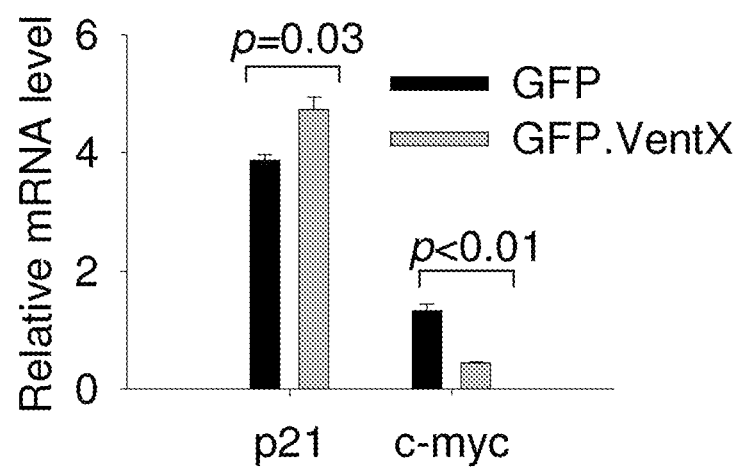
Figure 2:
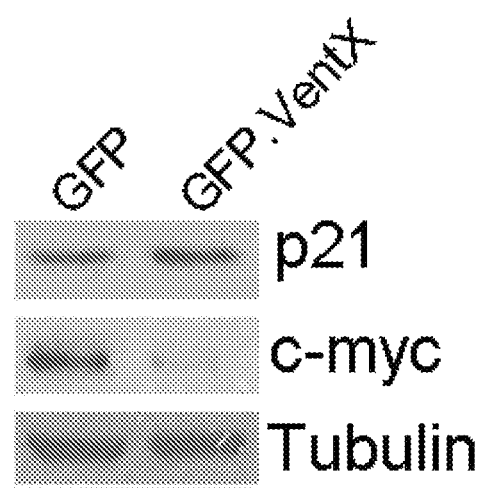
Figure 2:
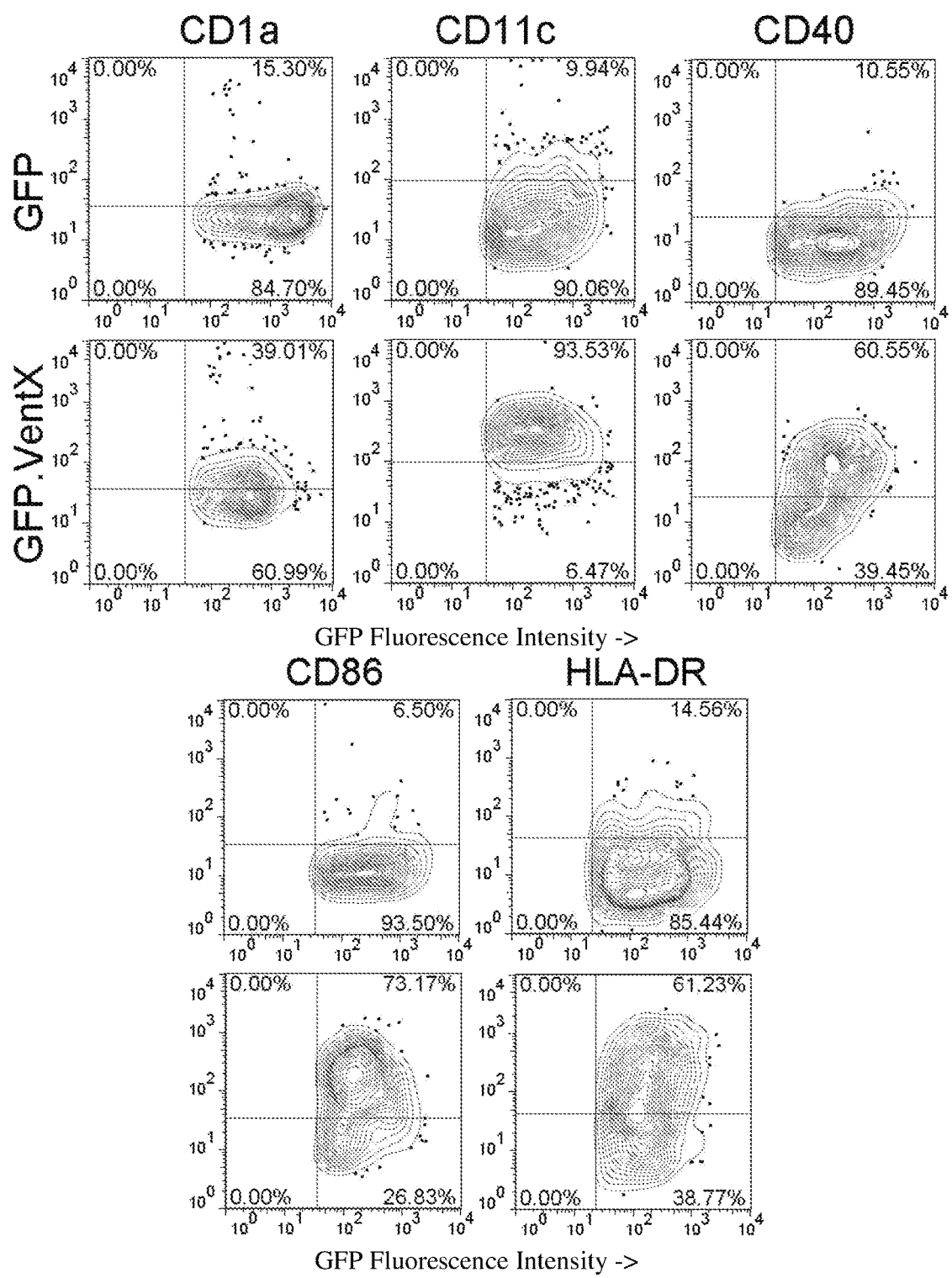
Figure 2:
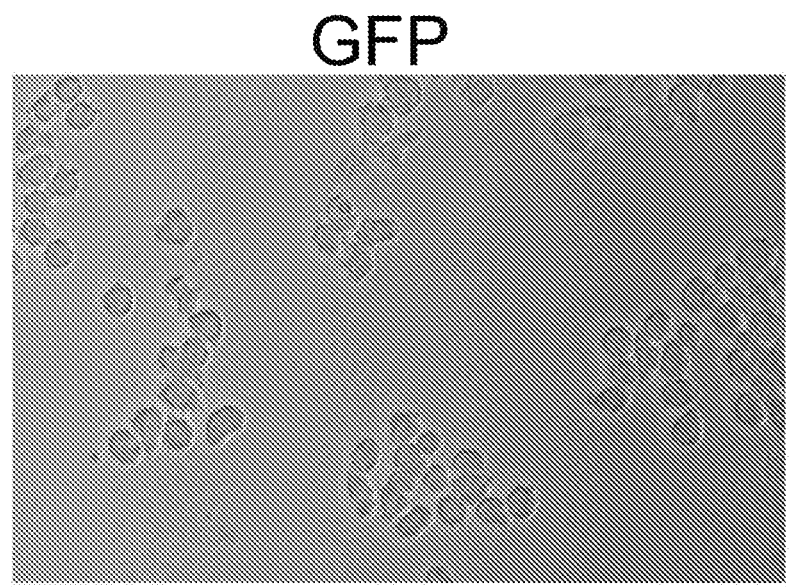
Figure 2:
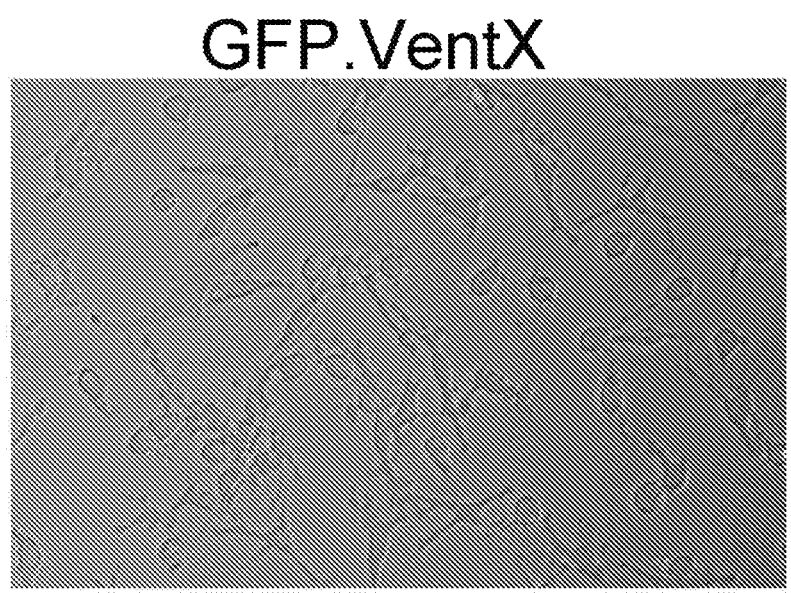

Human monocytic cell line THP1, under appropriate differentiation conditions, can be induced to differentiate into immature and mature DCs with phenotypic and functional properties similar to those of primary DCs. (Ogasawara, et al. 2009 *Biochem Biophys Res Commun* 389(3): p. 543-9; Menetrier-Caux, et al. 1998 *Blood* 92(12): p. 4778-91.) To further explore the effects of VentX on dendritic cell differentiation and its underlying mechanisms, stable THP1 cell lines were generated expressing GFP or GFP.VentX under the control of doxycycline-inducible promoter. VentX has been reported to function as an anti-proliferation and pro-differentiation transcriptional factor. (Wu, et al. 2011 *J Clin Invest* 121(7): p. 2599-613; Kamada, et al. 2008 *J Clin Invest* 118(6): p. 2269-80; Berges, et al. 2005 *Biochem Biophys Res Commun* 333(3): p. 896-907; Grassl, et al. 1999 *J Am Soc Nephrol* 10(7): p. 1466-77.) Thus, it was first examined whether overexpression of VentX could exert an inhibitory role on the proliferation of THP1 cells. Consistent with prior studies, expression of VentX in THP1 cells induced apparent growth inhibition (FIG. 2A) and G1 cell cycle arrest (FIG. 2B), which was associated with the down-regulation of c-myc and up-regulation of p21 expression by VentX (FIG. 2C-D). To determine the effects of VentX expression on DC differentiation of THP1 cells, a suboptimal induction condition was developed under which a mild differentiation of GFP transduced THP1 cells could be observed (FIG. 2E upper panel). Under this condition, overexpression of VentX significantly accelerated the DCs differentiation of THP1 cells. As shown in FIG. 2E, VentX transduced THP1 cells displayed a markedly increase of surface expression of CD1a, CD11c, CD40, CD86 and HLA-DR, indicating an enhanced DCs differentiation in these cells. The expression of CD36, CD64 and CD80 remained largely unchanged in VentX transduced THP1 cells. Strikingly, VentX transduced THP1 cells became adherent and flattened with extensive dendrite formation (FIG. 2F, right panel), resembling the morphology of DCs derived from primary monocytes. In contrast, no such morphological changes were observed in GFP transduced cells (FIG. 2F, left panel). Altogether, these results suggest that VentX may play a general role in DCs differentiation.

IL-6 Mediates VentX Regulation of DCs Differentiation

Figure 4:
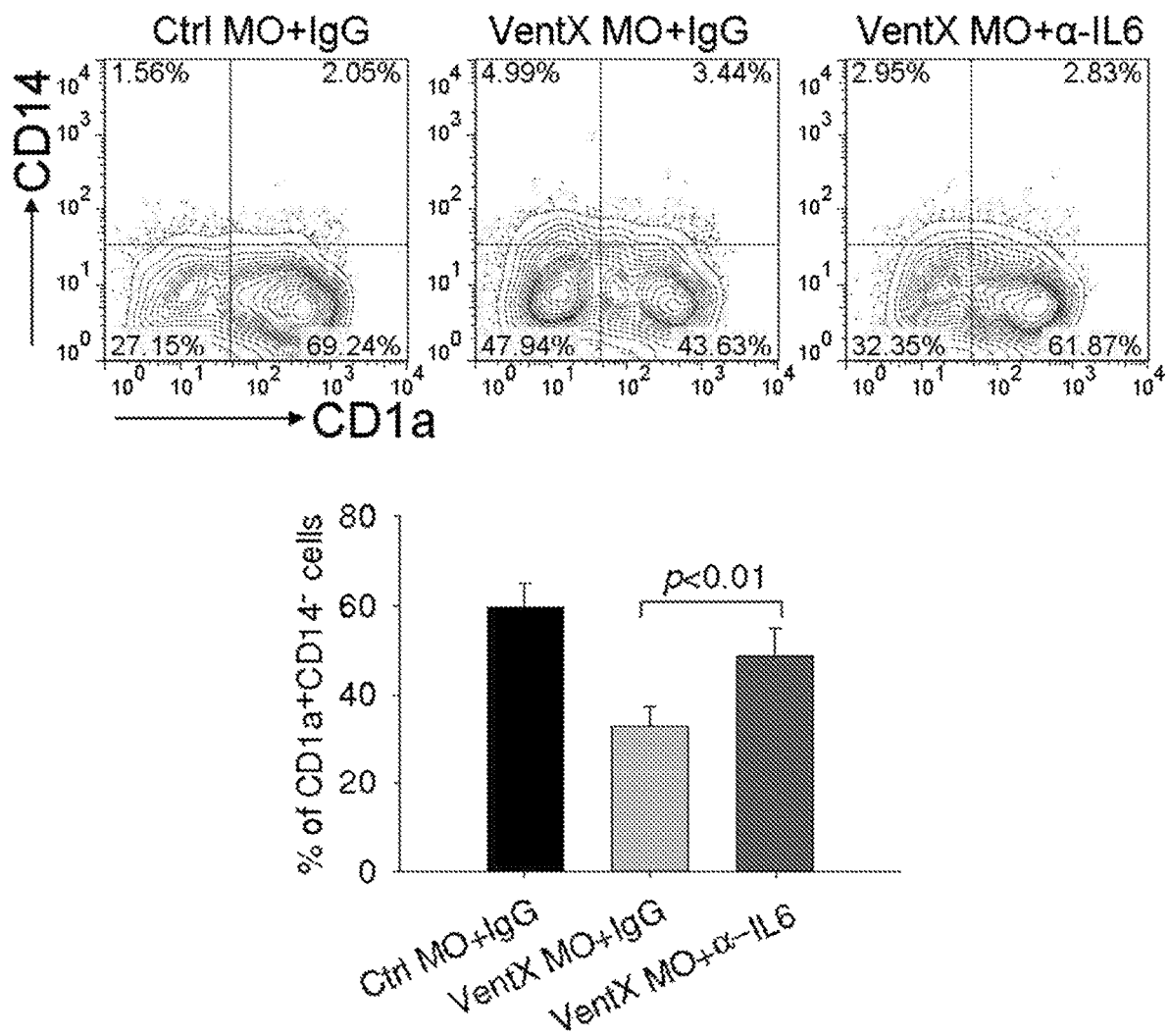
FIG. 4: Enhanced auotcrine IL6 contributes to differentiation defects in dendritic cells with VentX knockdown. Human primary monocytes were transfected with VentX MO or control MO as indicated. At second day, cytokines GM-CSF plus IL4 were added into culture medium together with neutralizing IL6 antibody or control immunoglobulin (IgG). Cells were harvested five days after cytokines addition and analyzed by flow cytometry (Left panel). The mean+SD of four separated experiments was shown in the right panel.

To elucidate the mechanisms underlying VentX regulated DCs differentiation and maturation, expression level of cytokines known to be important for DCs development was analyzed by reverse transcription PCR and intracellular staining. Whereas no apparent changes of IL1β, TNFα and IL10 expression were detected (data not shown), IL6 expression was consistently increased in cells transfected with VentX MO (FIGS. 3A and C). It has been shown that IL6 inhibits DC differentiation and maturation from both CD14$^+$ monocytes and CD34$^+$ progenitor cells. (Gabriele, et al. 2004 *Blood* 103(3): p. 980-7; Dendorfer, et al. 1994 *Mol Cell Biol* 14(7): p. 4443-54; Isshiki, et al. 1990 *Mol Cell Biol* 10(6): p. 2757-64; Libermann, et al. 1990 *Mol Cell Biol* 10(5): p. 2327-34.) To corroborate the results of knockdown experiments, the effect of ectopic expression of VentX on expression levels of IL6 was examined. Consistent with loss-of-function approach, overexpression of VentX reduced IL6 mRNA level (FIG. 3C) and inhibited IL6 production in primary monocytes (FIG. 3B). To determine whether VentX inhibits IL6 expression at transcriptional level, luciferase reporter assays with IL6 promoter was performed. The effect of VentX on the activity of 592 by IL6 promoter luciferase reporter and several deletion mutant constructs was assessed. (de Jong, et al. 1999 *J Leukoc Biol* 66(2): p. 201-4.) As shown in FIG. 3D, VentX significantly inhibited the −592 by IL6 promoter activity in primary monocytes. Previous studies have delineated several functional cis-regulatory elements in the human IL-6 promoter, including binding sites of AP1 (−283 to −277 bp), C/EBP (−158 to −145 bp and −87 to −76 bp) and NFκB (−75 to −63 bp)[33-36]. Interestingly, the activity of −80 by IL6 promoter, which contains only NFκB binding site[33], was suppressed by VentX to a degree similar to that of −592 by IL6 promoter (FIG. 3E), indicating that VentX may target NFκB binding site to regulate IL6 expression. To test this hypothesis, mutation analysis of the IL6 promoter was performed and it was found that mutation of NFκB binding site on the −80 by IL6 promoter abrogated the ability of VentX to inhibit the promoter reporter activity (FIG. 3F). To determine whether NFκB is involved in VentX regulated IL6 expression, the effects of VentX on the expression of NFκB and its interaction with IL6 promoter was examined. It was found that VentX does not affect the expression of NFκB (date not shown). However, using a chromatin immunoprecipitation assay, it was found that ectopic expression of VentX led to reduced binding of NFκB to the IL6 promoter (FIG. 3G), suggesting that VentX suppresses IL6 expression at transcriptional level through inhibiting NFκB interaction with IL6 promoter. To further investigate whether impaired DCs differentiation in VentX MO transfected monocytes could be ascribed to the increased IL6 secretion in these cells. To address this question, neutralizing antibody against IL6 was added to the culture medium of VentX MO transfected monocytes and differentiation of DCs was assessed through flow cytometry analysis of CD1a surface expression. As shown in FIG. 4, neutralizing IL6 activity with specific antibody significantly improved DCs differentiation defects in VentX MO transfected monocytes, indicating that VentX regulates DCs differentiation, at least partially, through modulating IL6 autocrine production.

VentX Regulates Dendritic Cells Maturation

Figure 5:
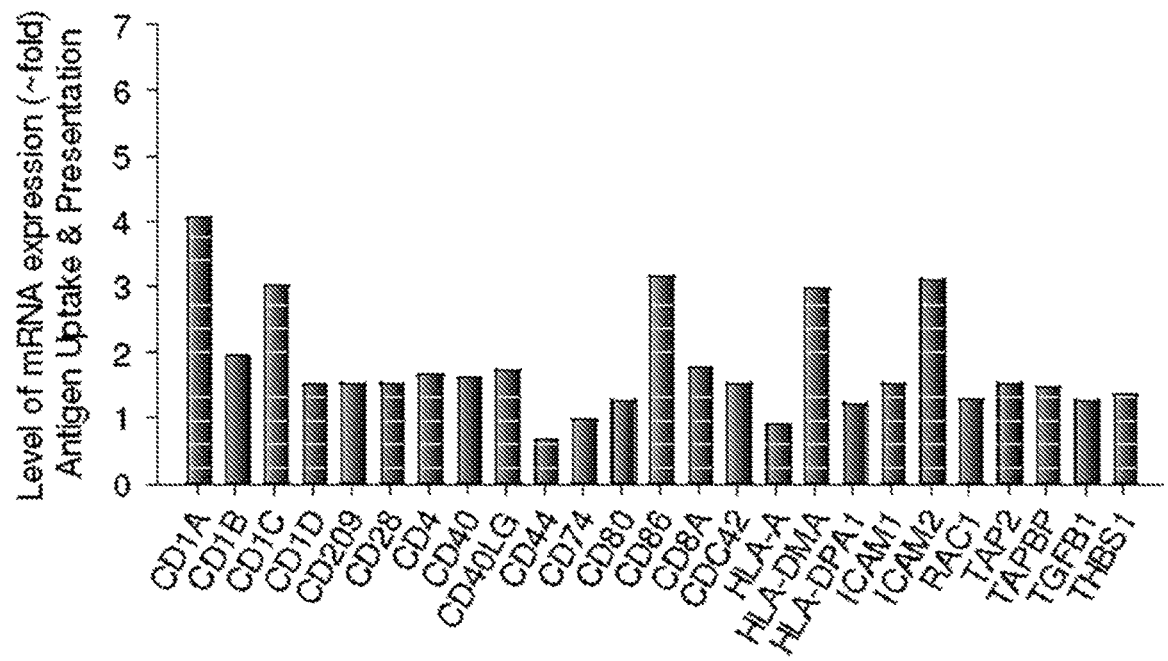
FIG. 5: PCR array analysis of dendritic cells that overexpress VentX. (A-E) Monocytes were transfected with pcDNA-GFP or pcDNA-GFP.VentX plasmids through electroporation. GM-CSF and IL4 were added to culture medium 2 hours later to induce DCs differentiation. At 3 days after transfection, LPS was added for overnight treatment and cells were harvested, sorted with GFP through flow cytometry. Total RNA was isolated and the mRNA levels of indicated genes were analyzed by PCR array. (F) The mRNA levels of selected genes were determined with different primer sets by real time PCR. Results shown are mean+SD of triplicates from one of two independent experiments and the differences were significantly different between two groups ($p<0.05$) for all genes.
Figure 5:
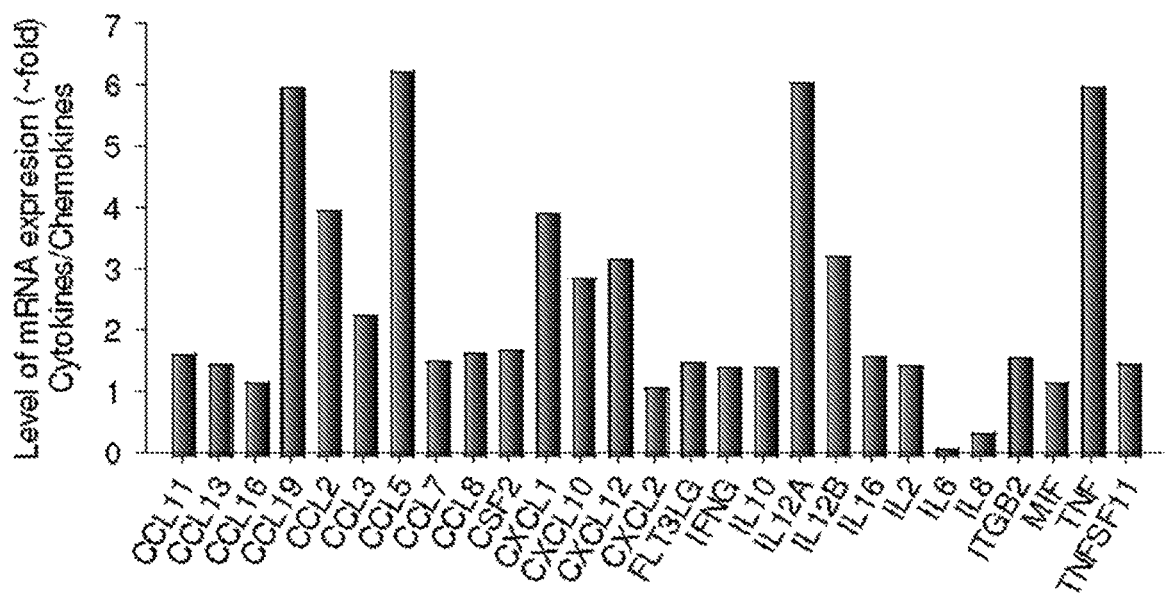
Figure 5:
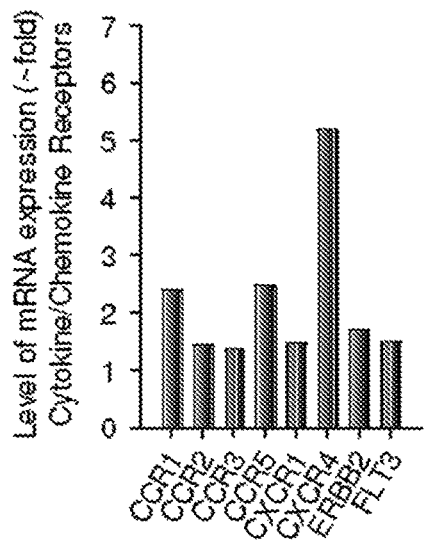
Figure 5:
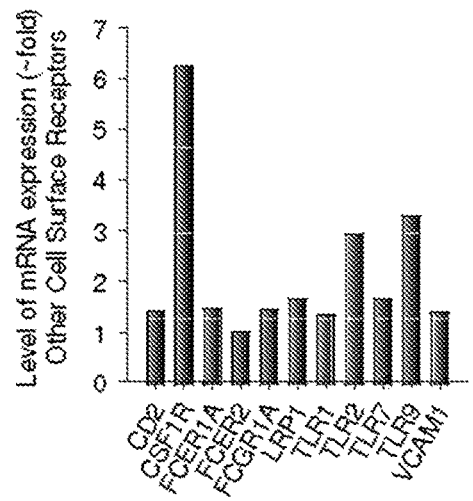
Figure 5:
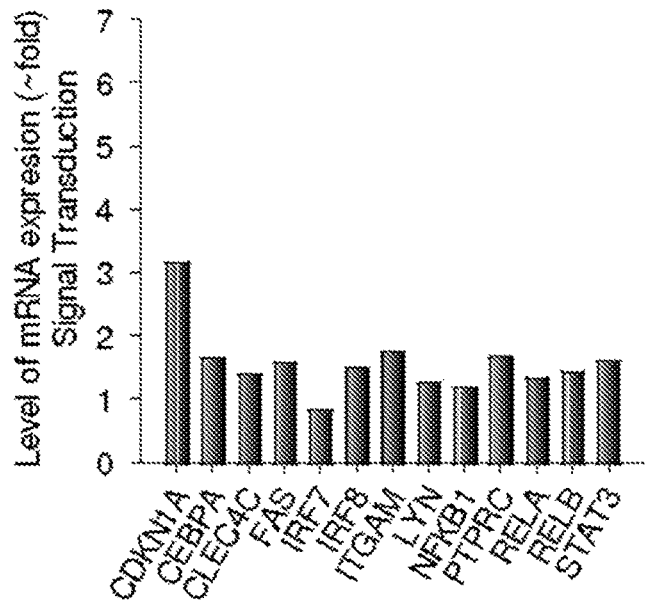
Figure 5:
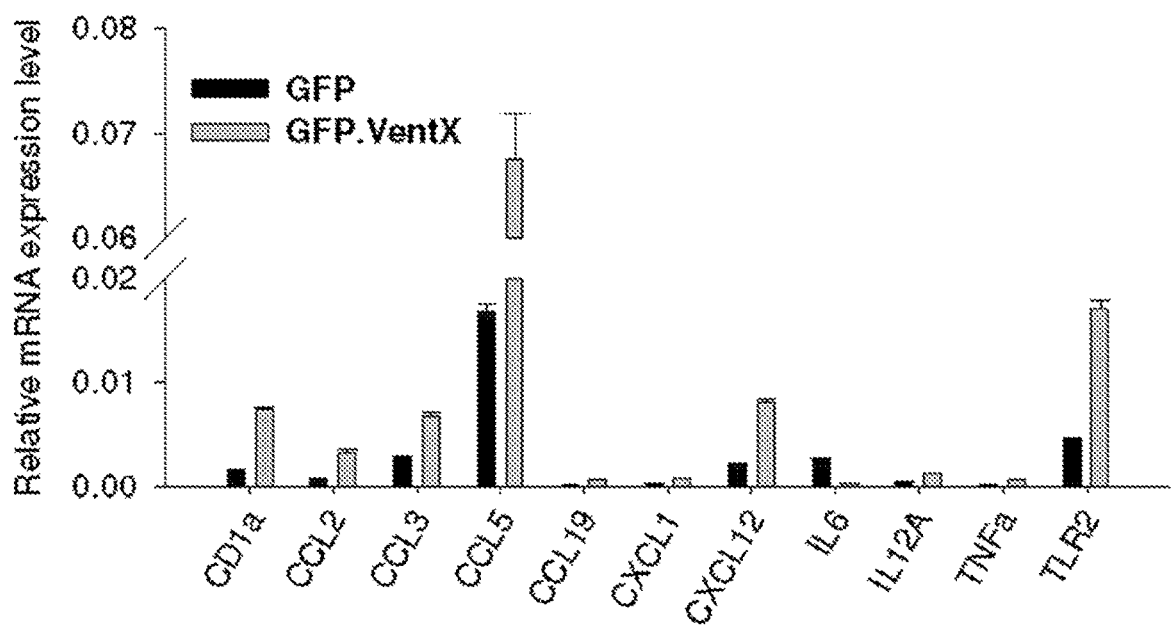

Upon stimulation with bacteria components, such as LPS, DCs undergo a process of maturation. To explore whether VentX plays a role in DC maturation, the effects of VentX on the changes of DCs gene expression profile during LPS induced maturation process was examined using a PCR array approach. The PCR array includes genes involved in antigen uptake and presentation, cytokines/chemokines and their receptors important for DC maturation. Cell surface receptors and signal transduction factors implicated in inflammation are also included in this array. As shown in FIG. 5A-E, overexpression of VentX induced up-regulation of a wide variety of genes, such as CD1 antigens, co-stimulatory factors CD80 and CD86, HLA molecules, proinflammatory cytokines IL12 and TNFα, chemokines CCL2 (MCP-1), CCL3(MIP-1α) and CCL5 (RANTES), chemokine receptors CCR5 and CXCR4, and Toll-like receptors (TLRs). In addition, the expressions of CSF1R (M-SCF receptor) and CDKN1A (p21) also increased as previously demonstrated. (Wu, et al. 2011 *J Biol Chem* 286(14): p. 12693-701; Wu, et al. 2011 *J Clin Invest* 121(7): p. 2599-613.) The results of PCR array were further verified by independent PRC reaction, using different sets of primers. As shown in FIG. 5F, independent quantitative PCR experiments produced consistent results as PCR array; therefore suggesting a potential role of VentX during DCs maturation process.

VentX Regulates DC Maturation During Intestinal Mucosal Inflammation

Figure 6:
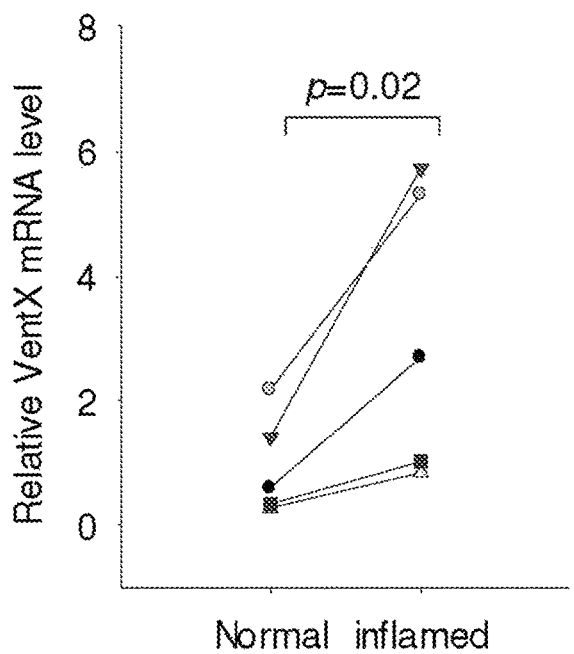
FIG. 6: VentX is required for the maturation of lamina propria DCs. (A) LPDCs were isolated from inflamed and non-inflamed intestinal mucosa of five IBD patients. VentX level was determined with real time PCR. (B) LPDCs were transfected with siRNA targeting VentX or control GFP through electroporation followed by culturing in medium for two days. Then cells were stimulated with LPS for overnight to induce maturation and harvested for flow cytometry analysis of surface markers and intracellular cytokines/chemokines. Filled histograms indicate siGFP transfection. (C) Bar graph shows the mean fluorescence intensity (MFI) of four different experiments in (B). Results are expressed as the percentage of MFI normalized to control. The differences were significantly different between two groups (p<0.05) except CD83, which is not significant (N.S). (D) LPDCs transfected with siGFP or siVentX were analyzed for the mRNA expression levels of indicated genes. The differences were significantly different between two groups (p<0.05) except CCL19 and CXCL1. (E) Knockdown of VentX impaired DCs capability to stimulate allogenic T cells proliferation in a mix lymphocytes reaction. (F) DCs were treated with prednisolone (10 µg/ml) for 48 hours or mock treated, and VentX level was determined with real time PCR. (G) DCs were transfected with GFP or VentX and treated with prednisolone as indicated. LPS was added 24 hours later and cells were harvested at 48 hours after transfection to analyze the mRNA levels of CCL3, CCL5, IL12A and TNFα. Results shown are mean+SD of triplicates from one of two independent experiments.
Figure 6:
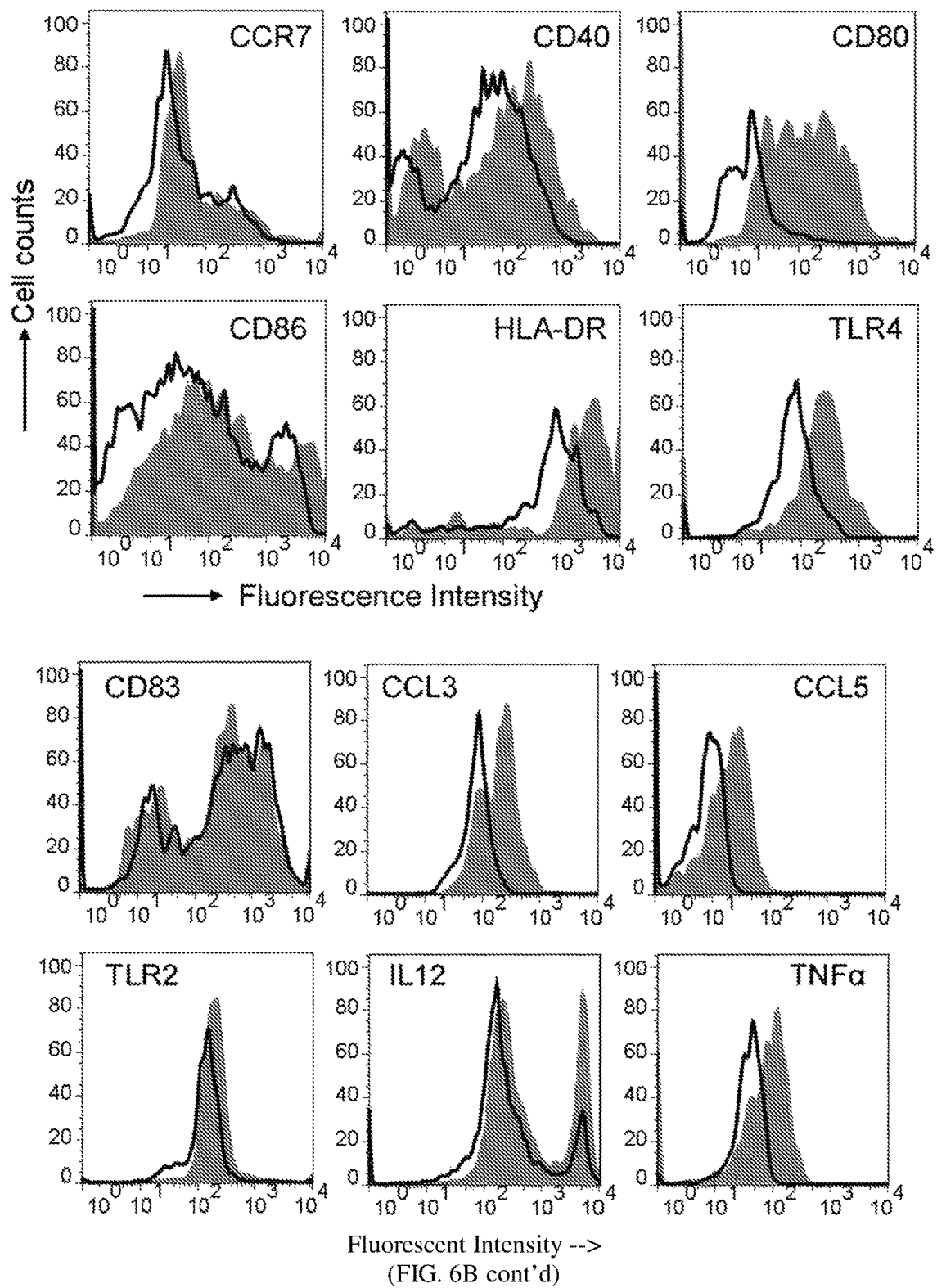
Figure 6:
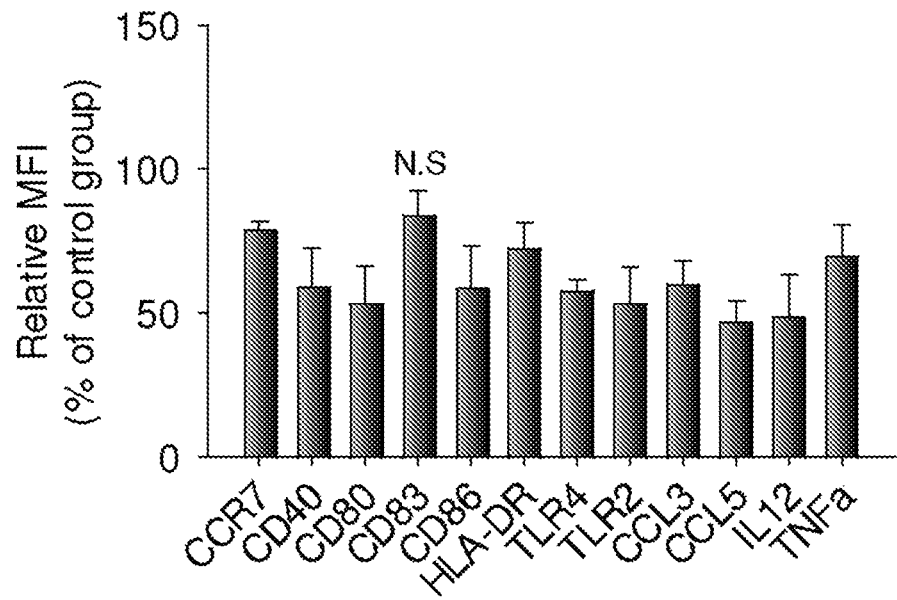
Figure 6:
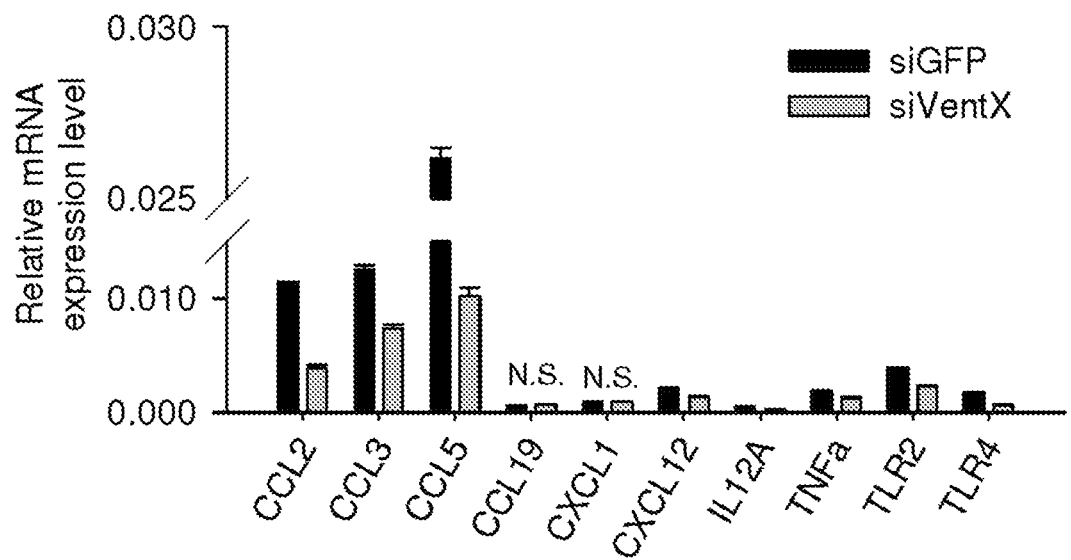
Figure 6:
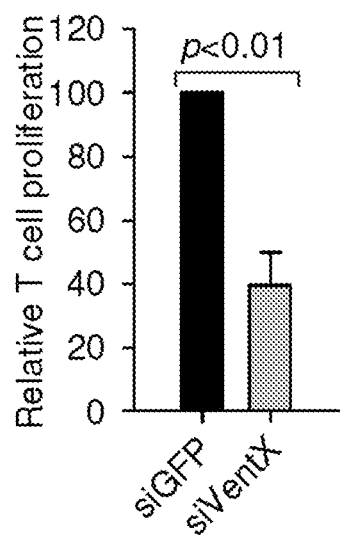
Figure 6:
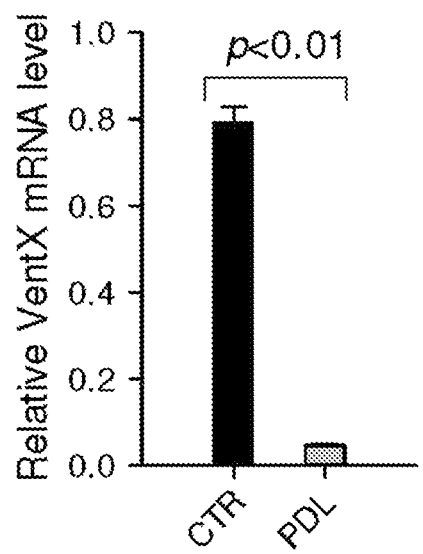
Figure 6:
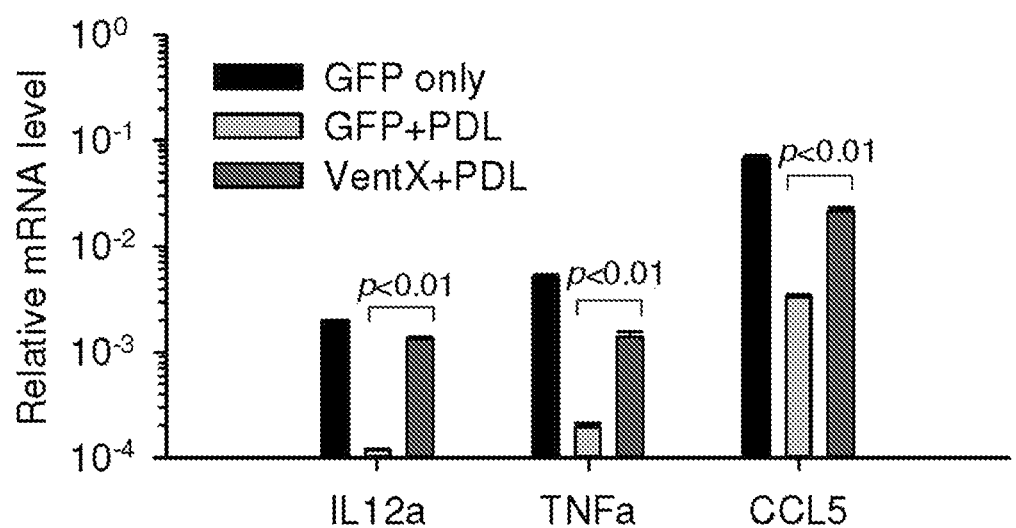

Aberrant activation of DCs has been implicated in mucosal inflammation in pathogenesis of inflammatory bowel diseases. To address the question, intestinal lamina propria DCs (LPDCs) were isolated from inflamed mucosal as well normal mucosa of patients with ulcerative colitis and Crohn's disease. VetnX expression levels in these DCs were determined by RT-PCR methods. As shown in FIG. 6A, VentX expression levels were significantly elevated in LPDCs from inflamed area in comparison with LPDCs from non-inflamed area (FIG. 6A). To determine whether the elevated expression of VentX is relevant to the aberrant activation of DCs, the effects of VentX knockdown on maturation and activation of LPDCs were tested. As shown in FIG. 6B-C, among the cell surface markers examined, knockdown of VentX in LPDCs significantly down-regulated expression of co-stimulatory factors CD40, CD80 and CD86, chemokine receptor CCR7, and pattern recognition receptors TLR2 and TLR4, which have previously been shown to be upregulated in DCs from inflamed intestinal mucosa of IBD patients. Expression of CD83 was unaffected by VentX knockdown. Intracellular staining demonstrated that LPDCs with VentX knockdown produced less inflammatory cytokines IL12, TNFα and chemokines CCL3, CCL5. Consistently, reverse transcription PCR revealed a significant decrease of mRNA level for CCL2, CCL3, CCL5, CXCL12, IL12, TNFα and TLRs in LPDCs cells with VentX knockdown in comparison with control LPDCs cells (FIG. 6D). In addition to the phenotype characterization, functional analysis showed that VentX knockdown in LPDCs cells significantly impaired the ability of DCs to stimulate primary T cells proliferation (FIG. 6E) Immune suppressants, such as corticosteroid, remain as the main treatment modality in managing mucosal inflammation in moderate to severe IBD patients and have been reported to modulate DCs maturation and function. (de Jong, et al. 1999 *J Leukoc Biol* 66(2): p. 201-4 Piemonti, et al. 1999 *J Immunol* 162(11): p. 6473-81.) To determine whether VentX might be a downstream target of steroids treatment in IBD, VentX expression levels were examined in LPDCs treated with prednisolone in vitro. As shown in FIG. 6F, steroid treatment dramatically decreased VentX expression in LPDCs, as well as the expression of pro-inflammatory cytokines, such as the IL2, TNF, CCL5 (FIG. 6G). When VentX was ectopic expressed in DCs, the inhibitory effect of corticosteroid on the expression of pro-inflammatory cytokines was significantly diminished, suggesting that steroids exert its anti-inflammatory in part through down-regulating VentX expression in DCs.

Experimental

Materials and Methods

Human Primary Cells Isolation and Treatment

Peripheral blood mononuclear cells (PBMC) from healthy adult donors at Dana-Farber Cancer Institute were isolated by Ficoll density gradient centrifugation. CD14$^+$ monocytes were purified from PBMCs using anti-CD14 antibody coated magnetic microbeads (Miltenyi Biotec, Auburn, Calif.). Monocytes were cultured in 12-well plates at 1×10$^6$ cells/ml with RPMI 1640 medium containing 10% fetal bovine serum (FBS), GM-CSF (100 ng/ml) and IL4 (20 ng/ml) (PeproTech, Rocky Hill, N.J.). Cytokines were added to cultures every 2 or 3 days for a total of 5 days to induce dendritic cells differentiation. Neutralizing antibody against IL6 was purchased from R&D Systems (Minneapolis, Minn.) and used at daily dose of 2.5 µg/ml. Intestinal mucosa was obtained from surgically resected specimens from patients diagnosed with inflammatory bowel diseases including Crohn's disease and ulcerative colitis. Specimens were taken from both inflamed and non-inflamed mucosa and were confirmed macroscopically and microscopically. Lamina propria mononuclear cells were isolated using previously described techniques. (Dillon, et al. 2010 *J Immunol* 184(12): p. 6612-21; Kamada, et al. 2008 *J Clin Invest* 118(6): p. 2269-80.) LPDCs were purified as the fraction of CD19$^-$CD1c$^+$ cells with magnetic microbeads (Miltenyi Biotec). To promote maturation of DCs, 100 ng/ml of *E Coli* LPS (Sigma-Aldrich) was added to the medium and further cultured for 24 hours. Experiments with human materials were performed in accordance with guidelines approved by the institutional review committee of Brigham and Women's Hospital.

VentX Knockdown

Human primary monocytes were transfected with Morpholino (MO) antisense oligonucleotides using the Human Monocyte Nucleofector Kit (Lonza, Walkersville, Md.) according to the manufacturer's instructions. Briefly, 10×10$^6$ monocytes were re-suspended into 100 µl nucleofector solution with 2.5 nmol of either VentX MO oligonucleotides (VentX MO: 5'-TACTCAACCCTGACATA-GAGGGTAA-3' or VentX MO-2: 5'-GAGCCCGGTTTGCATACACGGCTAA-3') or a standard control MO oligonucleotides and electroporated with the Nucleofector II Device (Lonza). Cells were then immediately removed from the device and incubated overnight with 1 ml pre-warmed Human Monocyte Nucleofector Medium containing 2 mM glutamine and 10% FBS. Cells were then re-suspended into complete RPMI medium and treated with appropriate cytokines to induce differentiation into DCs. All the MO oligonucleotides were ordered from Gene Tools (Philomath, Oreg.). LPDCs were transfected with siRNA targeting VentX as described in a previous study. (Wu, et al. 2011 *J Clin Invest* 121(7): p. 2599-613.)

Generation of THP1 Cell Line Conditionally Expressing VentX

Human monocytic leukemia cell line THP1 was obtained from American Type Culture Collection (ATCC; Manassas, Va.). The doxycycline inducible retroviruses expressing GFP.VentX or GFP have been described in a previous study. (Wu, et al. 2011 *J Clin Invest* 121(7): p. 2599-613.) The THP1 cell line conditionally expressing GFP.VentX was generated through co-transduction of pRetroX-GFP.VentX and pRetroX-Tet-On Advanced retroviruses and GFP.VentX positive cells were sorted by FACSAria high-speed sorter (BD Bioscience, San Jose, Calif.) after incubation with 1.0 µg/ml doxycycline for 24 hours (Dana-Farber Cancer Institute Flow Cytometry Core Facility). Sorted cells were then maintained in RPMI 1640 medium in the absence of doxycycline. The THP1 cell line conditionally expressing GFP was generated similarly as a control. To induce differentiation of THP1 cells toward DCs, cells were treated with the cytokines cocktail as described previously with some modifications. (Berges, et al. 2005 *Biochem Biophys Res Commun* 333(3): p. 896-907.) Briefly, cell were grown in 12-well plate in RPMI1640 medium supplemented with 10% FBS, 100 ng/ml GM-CSF, 50 ng/ml IL4 and TNF-α, 100 ng/ml Ionomycin for 2 days. Under this sub-optimal condition, only mild DCs differentiation was observed in GFP-expressing THP1 cells, which allowed us to determine the effect of VentX expression on the DCs differentiation in this model cell line.

FACS Analysis

Phenotypic analyses of DCs and THP1 cells were performed with flow cytometry after immunostaining of cells with fluorescence dye conjugated antibodies (eBioscience, San Diego, Calif.). The following FITC or PE conjugated antibodies were used: anti-CD1a, CD1b, CD1c, CD11c, CD14, CD16, CD36, CD40, CD64, CD80, CD83, CD86, CD116, CCR7, HLA-DR, TLR2 and TLR4. Intracellular staining of CCL3, CCL5, IL6 and IL12 p70 and TNFα were performed with PE-conjugated antibodies following the protocol provided by manufacture. Isotype control staining was performed in parallel for all experiments. Cell cycle analysis was carried out by Propidium Iodide (PI) staining. Stained cells were analyzed with FACScan flow cytometer (BD Bioscience) using FlowJo software. Results are expressed as the percentage of positive cells or mean fluorescence intensity (MFI) values after subtraction of the MFI obtained from the isotype control antibody.

Luciferase Reporter Assay

The −592 by fragment of human IL6 promoter region was amplified with forward primer: 5'-GTAACGCGTTTCTA-CAACAGCCGCTCACAG-3' and reverse primer: 5'-GA-TAGAGCTTCTCTTTCGTTC-3'. The −225 by and −80 by promoters were amplified with the same reverse primer and the following forward primers respectively: 5'-GTAACGCGTCAATGACGACCTAAGCTGCAC-3' and 5'-GTAACGCGTGTGGGATTTTCCCATGAGTC-3'. The amplified products were digested with restriction enzymes Mlu I and Xho I, and digested fragments were subsequently cloned into pGL3 luciferase reporter. Transfection of reporter plasmid with pcDNA-VentX plasmid or control pcDNA-GFP plasmid into primary monocytes was carried out through electroporation. Reporter plasmid was also transfected into U2OS cells which stably express tetracycline-inducible VentX[18] and reporter activity was evaluated in the absence or presence of tetracycline. 10 ng Renilla luciferase plasmid was included for each transfection to normalize reporter activity. Cells were harvested at 48 hours after transfection or addition of tetracycline and analyzed with Dual-Luciferase Reporter Assay System (Promega, Madison, Wis.). Mutation of NFκB binding site of luciferase reporters was achieved through QuikChange® Site-Directed Mutagenesis Kit from Stratagene (Santa Clara, Calif.).The wild type NFκB binding sequence 5'-GGGATTTTCC-3' was mutated to 5'-GGGATTTTAG-3' as reported previously. (Grassl, et al. 1999 *J Am Soc Nephrol* 10(7): p. 1466-77.)

ChIP Assay

THP1 cell lines conditionally expressing GFP or GFP.VentX were employed to detect if VentX expression impairs the NFκB binding to IL6 promoter region. Cells were treated with 1.0 µg/ml doxycycline for 2 days and harvested for chromatin immunoprecipitation (ChIP) assay. The ChIP procedure was performed with SimpleChIP® Enzymatic Chromatin IP Kit from Cell Signaling (Danvers, Mass.) following the manufacturer's instructions. The NFκB/p65 antibody (Cell Signaling) was used for the immunoprecipitation. Human IL6 promoter region containing the NFκB binding site was amplified by quantitative PCR with forward primer: 5'-GGACGTCACATTGCACAATC-3' and reverse primer: 5'-GCCTCAGACATCTCCAGTCC-3'.

PCR Array, Real Time-PCR, Western Blot and Mixed Lymphocyte Reaction

Dendritic & Antigen Presenting Cell PCR Array was purchased from SABiosciences (Valencia, Calif.). Real time PCR was performed on a LightCycler® (480 Real-Time PCR System; Roche, Indianapolis, Ind.). Western blotting analysis was conducted as described in a prior study. (Wu, et al. 2011 *J Clin Invest* 121(7): p. 2599-613.) Primary antibodies against p21 and c-myc were from Cell Signaling, and anti-VentX antibody was purchased from Abcam (Boston, Mass.). Mixed lymphocyte reaction was performed as described previously except that BrdU was added to culture to determine T cells proliferation. (Wu, et al. 2011 *J Clin Invest* 121(7): p. 2599-613.) Incorporated BrdU was detected with PE-conjugated anti-BrdU antibody and analyzed with flow cytometry.

Statistical Analysis

The student's t-test was used to calculate statistical significance and p<0.05 was considered statistically significant.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of embodiments disclosed herein, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor the embodiments disclosed herein as the preferred disclosure.

EQUIVALENTS

The representative examples are intended to help illustrate the aspects, and are not intended to, nor should they be construed to, limit the scope. Indeed, various modifications and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of embodiments disclosed herein in its various embodiments and equivalents thereof.

What is claimed is:

1. An in vitro method for differentiating monocytes into dendritic cells, comprising:
    introducing into the monocytes an expression construct encoding human VentX polypeptide, wherein the VentX polypeptide is overexpressed in the monocytes, and
    culturing the monocytes under conditions allowing differentiation of the monocytes into dendritic cells, whereby the monocytes differentiate into dendritic cells.

2. The method of claim 1, wherein the culturing step includes culturing the monocytes in a medium containing GM-CSF and IL-4.

* * * * *